United States Patent
Rice et al.

(10) Patent No.: US 8,480,834 B2
(45) Date of Patent: *Jul. 9, 2013

(54) AUTOMATIC LABELING AND PACKAGING SYSTEM LABEL FOLDING AND APPLICATION

(75) Inventors: Dennis Wayne Rice, Flanders, NJ (US); James G. McErlean, Allendale, NJ (US); E. Christian Hess, Flanders, NJ (US); Andrew P. Booler, Kitchener (CA); Allen Petten, Cambridge (CA); P. Thomas Shupert, Parkton, MD (US); Michael Joseph Szesko, Freehold, NJ (US); Orlando Vidal, Lumberton, NJ (US); Mark A. Detri, Lafayette, NJ (US)

(73) Assignee: Medco Health Solutions, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/367,786

(22) Filed: Feb. 7, 2012

(65) Prior Publication Data

US 2012/0312450 A1 Dec. 13, 2012

Related U.S. Application Data

(60) Continuation of application No. 12/190,167, filed on Aug. 12, 2008, now Pat. No. 8,110,057, which is a division of application No. 10/634,990, filed on Aug. 6, 2003, now Pat. No. 7,409,977, which is a continuation-in-part of application No. 10/215,249, filed on Aug. 9, 2002, now Pat. No. 6,892,512.

(60) Provisional application No. 60/401,340, filed on Aug. 7, 2002.

(51) Int. Cl.
*B65C 3/16* (2006.01)
*B29C 51/16* (2006.01)
*B29C 65/00* (2006.01)
*B31B 1/60* (2006.01)
*B32B 37/00* (2006.01)

(52) U.S. Cl.
USPC ............. 156/215; 156/212; 156/196; 156/60; 156/1

(58) Field of Classification Search
USPC ................................ 156/215, 212, 196, 60, 1
See application file for complete search history.

(56) References Cited

U.S. PATENT DOCUMENTS

| | | | | |
|---|---|---|---|---|
| 4,502,910 A * | 3/1985 | Voltmer et al. | ............... | 156/361 |
| 6,273,411 B1 * | 8/2001 | Vijuk | ............................... | 270/37 |
| 6,976,628 B2 * | 12/2005 | Krupa | ...................... | 235/462.08 |

* cited by examiner

*Primary Examiner* — Christopher Schatz
*Assistant Examiner* — Matthew Hoover
(74) *Attorney, Agent, or Firm* — Husch Blackwell LLP

(57) ABSTRACT

The method of labeling of a container including a medication includes, in at least one embodiment, reducing a size of the label using a label apparatus and reducing the label size using the label apparatus, applying a surface securing adhesive to at least one surface securing section of the label using an adhesive application apparatus, and attaching the at least one surface securing section of the label to the container with the securing adhesive. The method also includes applying a label securing adhesive to the label to maintain the label in the reduced orientation.

22 Claims, 25 Drawing Sheets

AUTOMATIC LABELING AND PACKAGING SYSTEM LABEL FOLDING AND APPLICATION

CROSS REFERENCE TO RELATED APPLICATIONS

This application is a continuation application of U.S. patent application Ser. No. 12/190,167, filed on Aug. 12, 2008, now U.S. Pat. No. 8,110,057, issued on Feb. 7, 2012, which is a divisional application of U.S. patent application Ser. No. 10/634,990 filed on Aug. 6, 2003, now U.S. Pat. No. 7,409,977, issued on Aug. 12, 2008 entitled "AUTOMATIC LABELING AND PACKAGING SYSTEM LABEL FOLDING AND APPLICATION", which is related to and is a continuation-in-part of U.S. patent application Ser. No. 10/215,249, filed on Aug. 9, 2002, now U.S. Pat. No. 6,892,512 issued on May 17, 2005, entitled "AUTOMATED PRESCRIPTION FILLING SYSTEM/METHOD WITH AUTOMATED LABELING AND PACKING SYSTEM/METHOD AND AUTOMATED ORDER CONSOLIDATION SYSTEM/METHOD", which claims priority from U.S. Provisional Application Ser. No. 60/401,340, filed on Aug. 7, 2002, all of which are incorporated herein by reference.

The present invention relates to a labeling system and, in particular, the present invention relates to a method and system for labeling medication containers using a label that is reduced in size.

BACKGROUND OF THE RELATED ART

In mail service pharmacies and large retail pharmacies, prescription drugs are dispensed in a high volume. For such services, it is known to use an automatic pill dispensing system to carry out the dispensing of the prescription drugs automatically at a rapid rate and to label pill containers, which can then be provided to the patient for whom the prescriptions were written.

U.S. Pat. No. 6,413,345 (Treleaven), which is incorporated herein by reference, discloses a method of forming a label for displaying information, which includes providing a release liner having an upper surface. Prior art FIG. 1 illustrates label 10, which includes leaflet 11 and laminate cover 50. Label 10 extends from leading edge 94 to trailing edge 92. Label 10 is releasably secured to release liner 12 by adhesive layer patch 70 and adhesive layer portion 52A. Each of adhesive layer 70 and adhesive layer 52A remain with label 10 when it is removed from release liner 12 and serve to secure label 10 to a container. An adhesive-free zone or gap 90 is defined between adhesive layer 70 and adhesive layer 52A and extends the width of the label. The provision of gap 90 facilitates application of the label to round containers.

Label 10 includes tear strip 60 and tear lines 58 and 64 which provide for access to and detachment of the various panels of leaflet 11. Leaflet 11 includes bottom panel 20, top panel 30, first interior panel 40, and additional interior panels 42. Top panel 30 and bottom panel 20 are joined along fold 66. Top panel 30 and first interior panel 40 are joined along the fold 65. Fold 66 forms a leading edge of the leaflet. Top panel 30 includes parallel, spaced apart tear lines 35A and 35B formed therein. Tear line 64 is formed along fold 65 (as shown) or, alternatively, in panel 40 adjacent fold 65. Top panel 30 includes marginal portion 32 extending between fold 66 and the adjacent edge 68 of interior panel 40. Bottom panel 20 includes marginal portion 22 extending between fold 66 and adjacent edge 168. Bottom panel 20 further includes marginal extended flap 24 extending outwardly beyond top panel 30. Suitable title indicia 33 is printed on the upper surface of top panel 30. Marginal extended flap 24 preferably extends at least one-half inch beyond the longest of the top and interior panels, and more preferably from about one-half to five-eighths of an inch. Indicia 127 such as "EXP:" and "LOT:" are printed on the upper surface of marginal extended flap 24. Indicia 23, preferably substantially identical to indicia 33, is disposed on the upper surface of bottom panel 20. Other suitable indicia 43, for example, instructions and warnings, are printed on panels 40, 42.

U.S. Pat. No. 6,511,569 (Nixon et al.), which is incorporated herein by reference, discloses an apparatus for in-line folding and affixing a self-adhesive label to an article, the label having a fold line thereacross defining a foldable portion and a cover portion of the label. As illustrated in prior art FIG. 2, the apparatus 100 includes a printing station 110, a label transfer grid 120, a folding station 140, first, second, and third air blast nozzles 150, 155, 158, respectively, and an affixing station 160.

The label transfer grid 120 includes an inner row 121 of rollers 121a and an outer row 122 of rollers 122a, wherein the rollers 122a of the outer row 122 are spaced from the rollers 121a of the inner row 121 by a sufficient distance to grip the tuck label therebetween and to convey the tuck label from the printing station 110 to the transfer station 160 along a generally upwardly-curved path.

Transfer grid 120 includes a first end 126A, located adjacent printing station 110, and a second end 120B, located adjacent affixing station 160. Generally, label transfer grid 120 conveys the label from the printing station 110, from which the label typically exits in a horizontal orientation, to the affixing station 160, wherein the label is in a vertical orientation to be affixed to the vertical sidewall surface 131 of the container 130. The label transfer grid 120, then, includes a generally upwardly-curved bend, by which the flexible label moves from a horizontal orientation to a vertical orientation for affixing to the container 130. However, the orientation of the label need not be altered by a bend in the grid 120, and the label may be of any orientation suitable to be affixed to the container 130 as it exits the grid 120. For example, if surface 131 of container 130 is horizontal, label should exit the grid 120 in an orientation suitable to be affixed to the horizontal surface of the container 130.

The outer row 122 of rollers 122a includes an opening 123 which is defined as an absence of one or more rollers in the outer row 122. Alternatively, the opening 123 may be defined by the spacing between two consecutively-spaced rollers 122a in the outer row 122, wherein the spacing between two consecutively-spaced rollers 122a is sufficient to permit the label to pass therebetween. Remaining rollers 122a are spaced to pass the label therealong and to convey the label through the grid 120.

The opening 123 is sized to allow the leading edge 123, that being in the preferred embodiment, the foldable portion 122 of the tuck label, to pass outwardly from within the grid 120, through the opening 123 and towards the folding station 140 as the label is conveyed through the generally upwardly-curved bend of the transfer grid 120. The third air blast nozzle 158 is positioned alongside the inner row 121 of rollers 121a and is directed towards the outer row 122 of rollers 122a to emit a stream of pressurized air through the grid 120, as shown generally by reference numeral 159. Air stream 159 urges the leading edge 123 of the foldable portion 122 of the label through the opening 123, to project from within the grid 120 and outwardly towards the folding station 140.

A conventional timing control circuit, such as a programmable logic controller, is provided with sensors and valves to signal the air blast 159 to urge the leading edge 123 of the foldable portion 122 of the label through the opening 123. Alternatively, rollers 121a, 122a may be driven by one or more stepper motors, in which case, air blast 159 may be controlled with reference to movement of the stepper motor (and, as such, by the location of the label in the grid 120), instead of by the programmable timing controller. Alternatively still, the air blast 159 may be a continuous stream of pressurized air being emitted from the air blast nozzle 158.

As the grid 120 conveys the label towards the second end thereof, forward movement of the label along the rollers 121a, 122a is diverted temporarily through the opening 123 towards the folding station 140. Forward movement of the label by the grid 120, then, advances the foldable portion 122 of the label further out of the grid 120.

Neither the Treleaven nor the Nixon et al. references relate to or disclose, for example, a method or system for size reduction of a patient label and adhesion of the label directly to an item. Further, neither Treleaven nor Nixon et al. relate to, for example, a container for a medication, where the label need not be self-adhesive. What is desired is, for example, a method and system for rolling a patient label, securing the patient label in the rolled position, and affixing the patient label to a medication using an adhesive. The invention, as described below, provides this, as well as other optimal features and/or functionality.

SUMMARY OF THE INVENTION

It is one feature and advantage of the present invention to provide a patient label that includes various information regarding the patient, the medication, and instructions for the use of the medication.

It is another, optional feature and advantage of the present invention to affix labels to a medication using a hot melt adhesive.

It is another, optional feature and advantage of the present invention to reduce the size of the patient label by folding, or otherwise reducing the size of, the patient label after the patient label has been printed.

It is another, optional feature and advantage of the present invention to utilize a transfer adhesive to secure the patient label in a folded, or otherwise reduced, position.

It is another, optional feature and advantage of the present invention to enable a patient to unfold the patient label while the patient label is still affixed to the medication container to read the information printed on the patient label.

It is another, optional feature and advantage of the present invention to enable the patient to resecure the patient label in the folded, or otherwise reduced, position, using the transfer adhesive.

It is another, optional feature and advantage of the present invention to ensure correct matching of a patient label to a medication through the use of barcodes.

It is another, optional feature and advantage of the present invention to provide a method and system for rejecting labels that are defective and/or are not correctly matched to a medication that is next in a production line.

These and other features and advantages of the present invention are achieved in a method of labeling a container including a medication. The method includes the sequential, non-sequential, and/or sequence independent steps of providing the label to a label apparatus. The method also includes applying a surface securing adhesive to the label, such that the label may be attached to the container. The method further includes affixing the label to the container.

In another embodiment of the present invention, a method of labeling of a container including a medication is provided. The container may be, for example, a bottle, box, and/or a package. A label provides information regarding the medication to a consumer. The method includes the sequential, non-sequential, and/or sequence independent steps of providing the label to a label apparatus and reducing the label size using the label apparatus. The label is prepared by the label apparatus for attachment to a surface of the container. The method also includes transporting the label from the label apparatus to an adhesive application apparatus. The method further includes applying a surface securing adhesive to at least one surface securing section of the label. The method also includes attaching the at least one surface securing section of the label to the container. The surface securing adhesive affixes the label to the container.

In another embodiment of the present invention, a method of labeling of a container including a medication, comprising at least one of a bottle and a package, with a label providing information regarding the medication to a consumer thereof, includes the sequential, non-sequential, or sequence independent the steps of providing the label to a label apparatus and reducing the label size using the label apparatus. The label is prepared by the label apparatus for attachment to a surface. The method also includes removing the label from the label apparatus and transporting the label from the label apparatus to an adhesive application apparatus. The method further includes applying a label securing adhesive to the label and attaching the label to the container. The label securing adhesive overhangs and edge of the label such that the label securing adhesive both secures the label in a reduced orientation and affixes the label to the container.

In another embodiment of the present invention, a system for labeling of a container including a medication is provided. The container may be, for example, a bottle, box, and/or a package. A label provides information regarding the medication to a consumer. The system includes a label reducing tool. The system also includes a label securing adhesive application device, which applies a label securing adhesive to the label such that the label is capable of being maintained in a reduced orientation. The system further includes a surface securing adhesive application device, which applies a surface securing adhesive to the label such that the label is capable of being attached to the container. The system also includes a label shuttle block. The label shuttle block removes the label from the label reducing tool and conveys the label from the label reducing tool to the surface securing adhesive application device.

In another embodiment of the present invention, a label including information relating to a medication is provided. The label is formed of a substrate having a first end and a second end, and dimensioned responsive to at least a length. The length is defined by the first end and the second end. The label also includes a first section on the substrate, which contains patient information. The label further includes a second section on the substrate, which contains usage instructions for the medication. The label also includes a third section on the substrate, which receives a transfer adhesive. The transfer adhesive secures the label in a reduced orientation. The label further includes a fourth section on the substrate, which receives a hot melt adhesive. The label also includes a fifth section on the substrate, which contains at least a barcode.

There has thus been outlined, rather broadly, the more important features of the invention and several, but not all, embodiments in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

DESCRIPTION OF THE PREFERRED EMBODIMENTS

Figure 1:
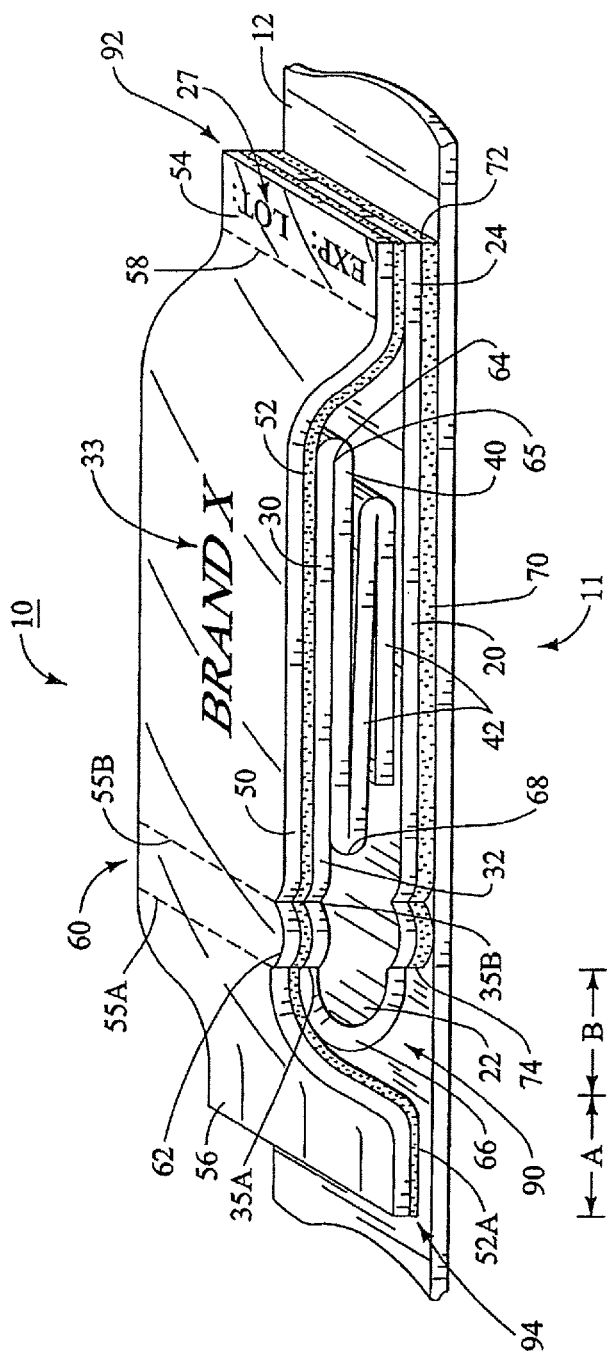
FIG. 1 illustrates a label according to the prior art.
Figure 2:
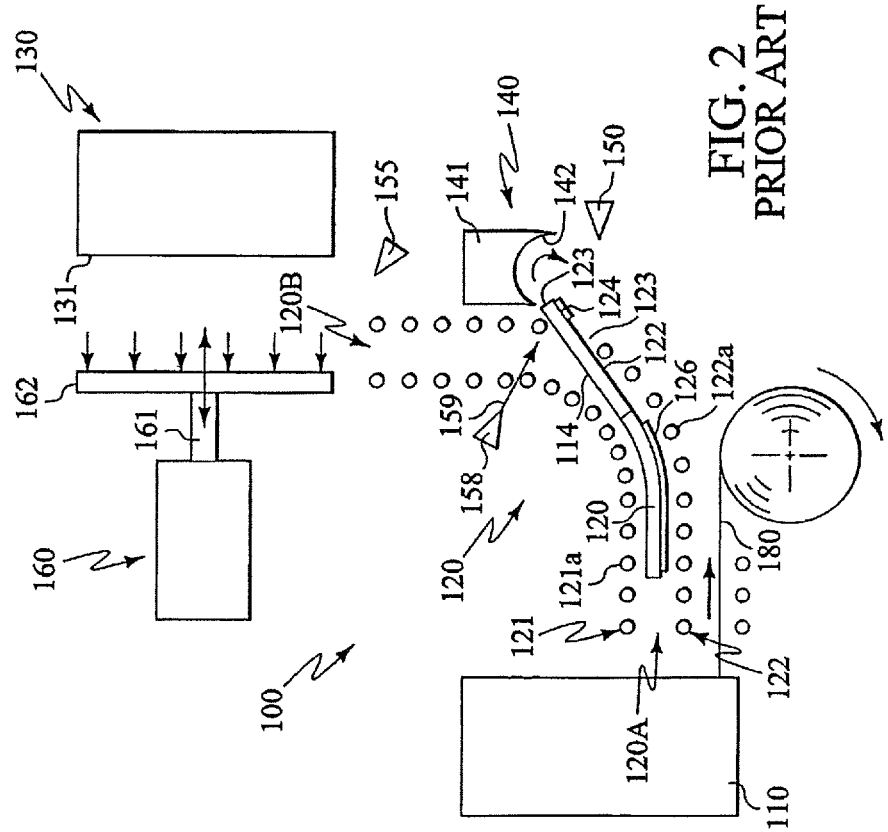
FIG. 2 illustrates a system of labeling an item according to the prior art.

Reference now will be made in detail to the presently preferred embodiments of the invention. Such embodiments are provided by way of explanation of the invention, which is not intended to be limited thereto. In fact, those of ordinary skill in the art may appreciate upon reading the present specification and viewing the present drawings that various modifications and variations can be made.

For example, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

FIGS. 3-6 illustrate an automated labeling system ("ALS"), designated generally by reference numeral 200. ALS 200 includes, for example: printer 202; label scanner 204; vacuum platen assembly 206; label folding tool 210; first label creasing wheels 208; spindle drive assembly 212; shuttle block track 214; shuttle block 216; label reject mechanism 218; rejected labels assembly 220; folded label scanner 228; transfer adhesive dispenser 246; main plate assembly 240; T-brackets 241; and printer mounting 243. The main components of ALS 200 are assembled on main plate assembly 240 and supported on printer mounting 243 using, for example, four T-brackets 241. The operation of ALS 200 is controlled by a system controller (not shown), for example, a standard programmable logic controller ("PLC").

Figure 3A:
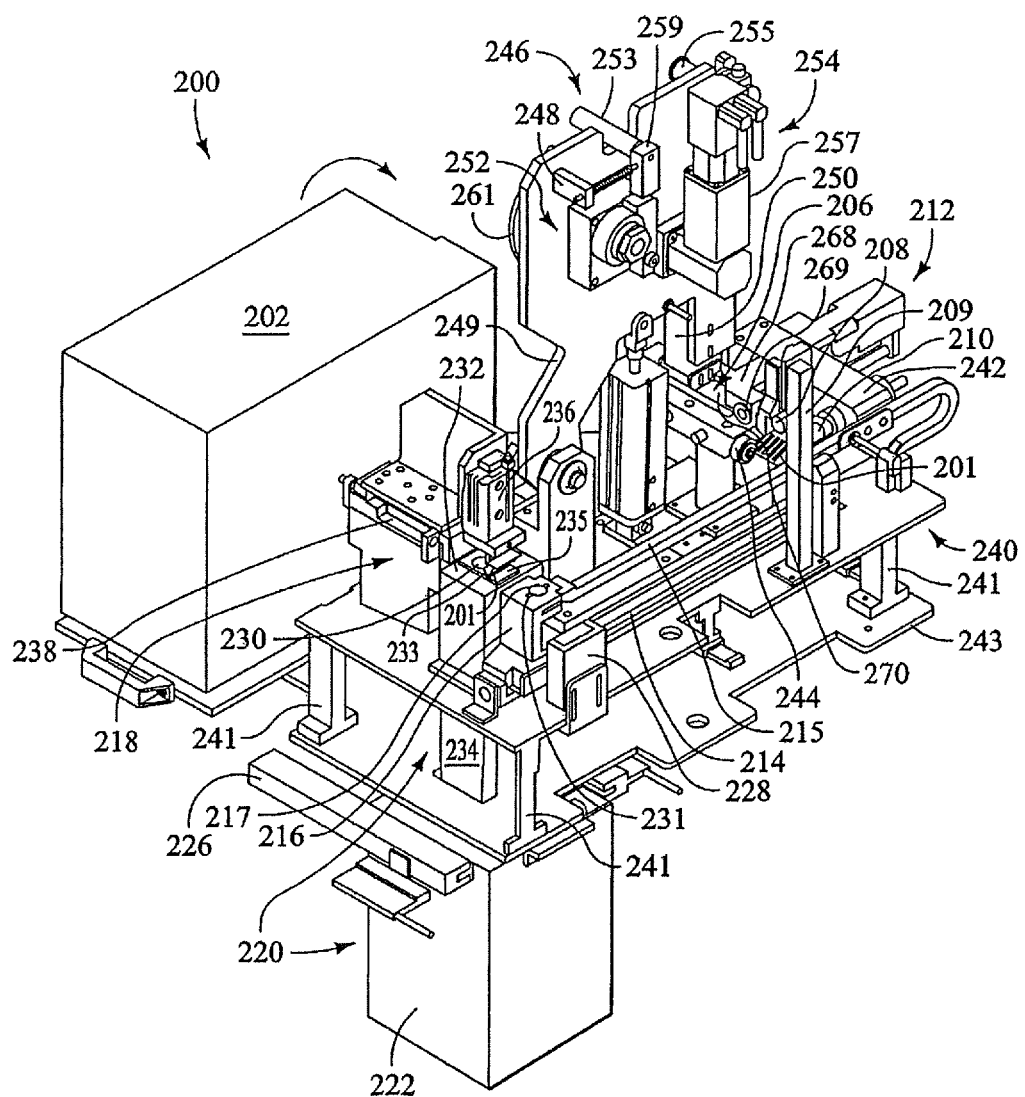
FIG. 3A illustrates an isometric view of an automated labeling system of the present invention.
Figure 3B:
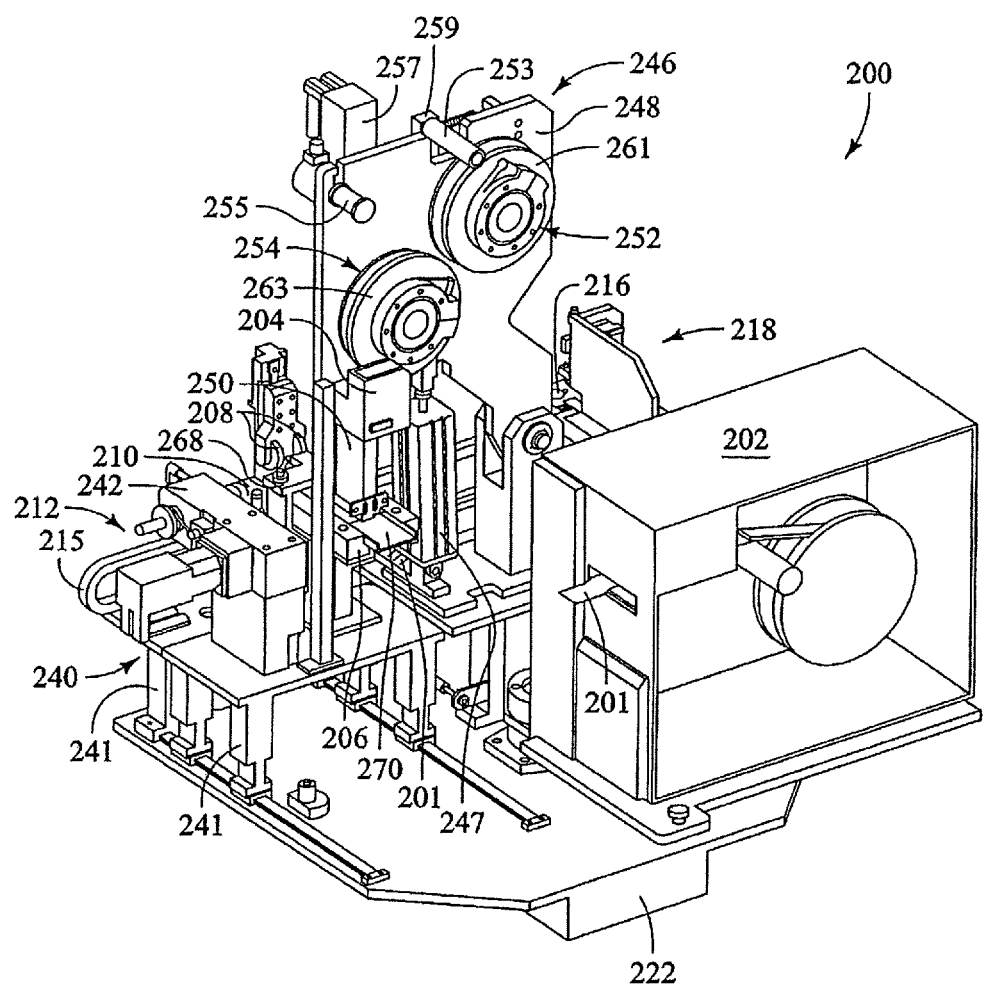
FIG. 3B illustrates a reverse isometric view of the automated labeling system of the present invention.
Figure 4:
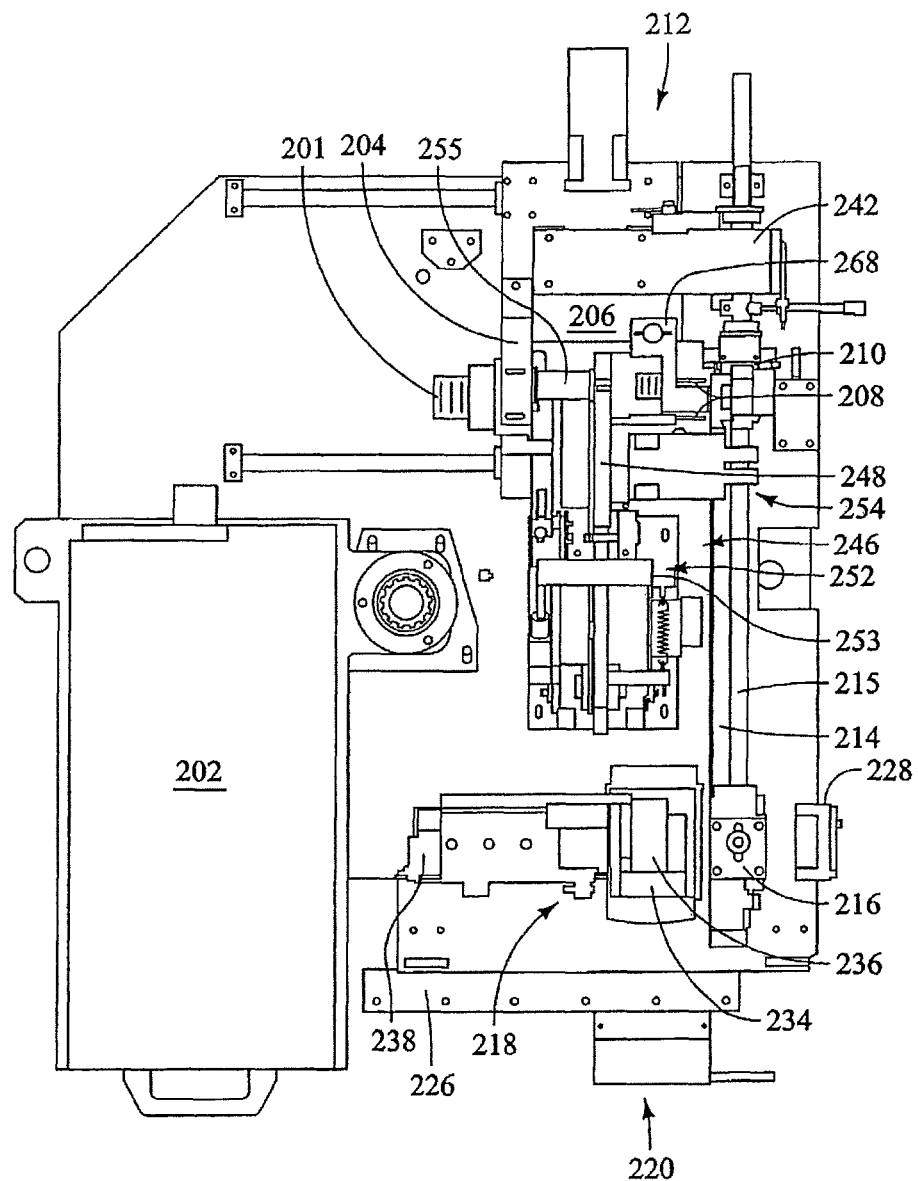
FIG. 4 illustrates an elevated view of the automated labeling system of the present invention.
Figure 5:
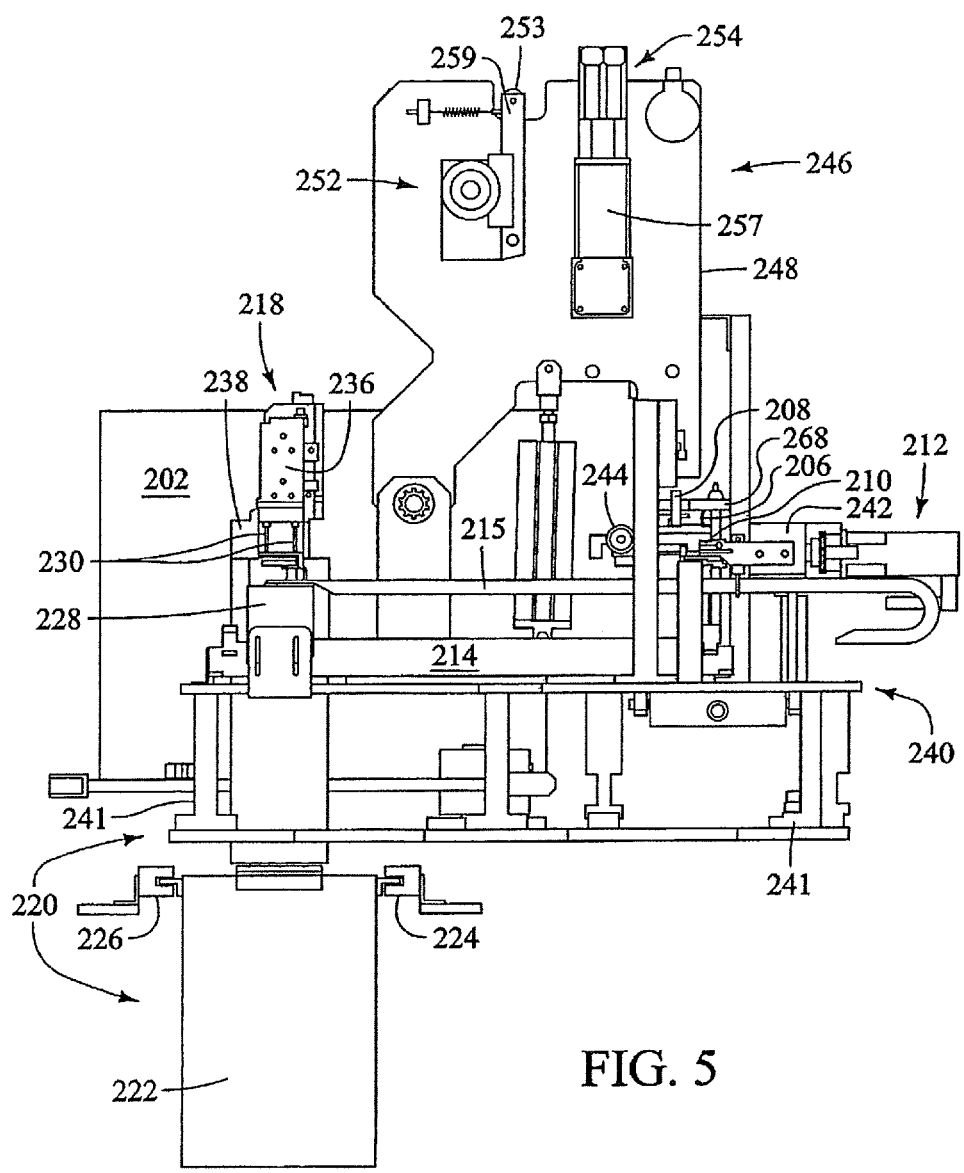
FIG. 5 illustrates an anterior view of the automated labeling system of the present invention.
Figure 6A:
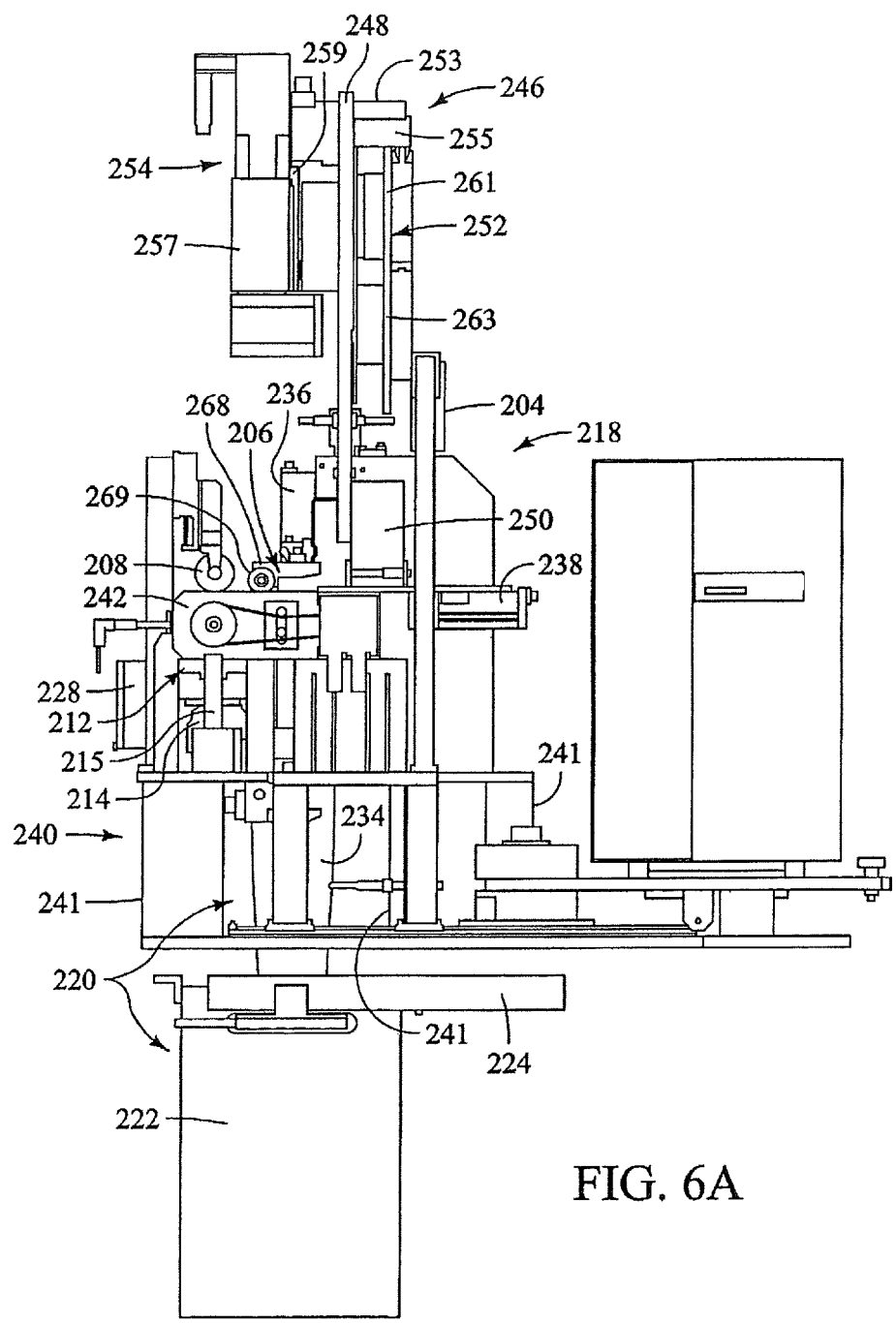
FIG. 6A illustrates a right side view of the automated labeling system of the present invention.
Figure 6B:
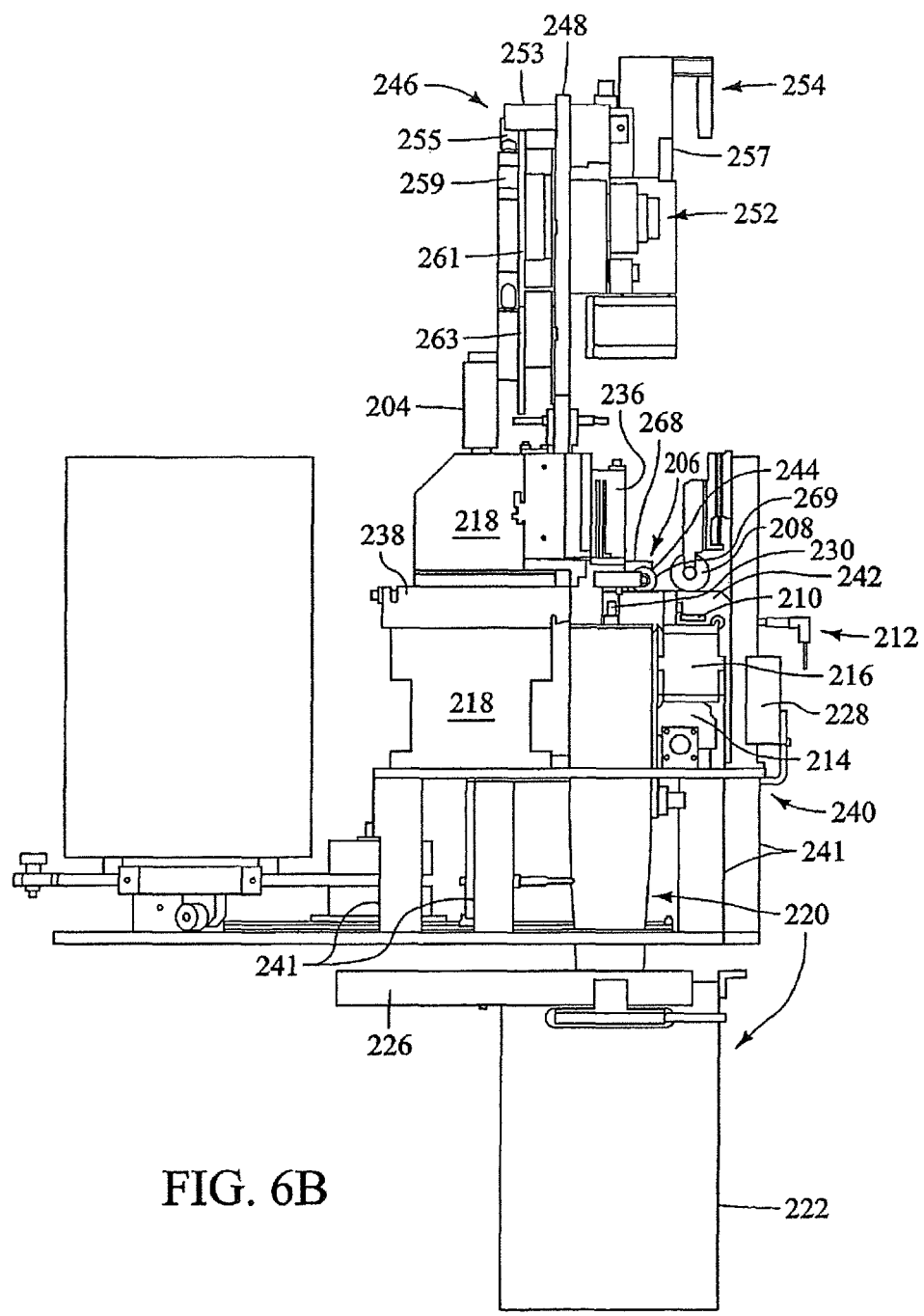
FIG. 6B illustrates a left side view of the automated labeling system of the present invention.

Printer 202 prints out a label 201 (as seen in FIG. 3B). During the operation, of ALS 200, printer 202 is rotated 90° from the position shown in FIGS. 3-6 such that the label opening of printer 202 is adjacent to vacuum platen assembly ("VPA") 206. Label scanner 204 scans a barcode printed on label 201 to identify a medication particular for which label 201 is intended. The system controller uses the barcode on label 201 to reference a file and/or a database, which stores information identifying medication containers and their appropriate labels. By scanning the barcode on label 201, the system controller can identify for which medication container label 201 is intended.

Label 201 is then fed into VPA 206. VPA 206 includes, for example: VPA upper guide 268; label hold down wheels 269 (FIGS. 3A, 6A, and 6B); vacuum platen top 270; and second label creasing wheel 244. Printer 202 prints out the full length of label 201. After the printing is completed, label 201 is fed into VPA 206 until label 201 lies on vacuum platen top 270 and a first end of label 201 lies across label folding tool 210. Label 201 may be, for example, 12 inches in length, and vacuum platen top 270 provides guidance to label 201 the entire length is fed out of printer 202.

Vacuum platen top 270 has a plurality of vacuum holes 271 (see FIG. 7) connected through a plurality of vacuum plenums (not shown) through which a vacuum may optionally be applied to label 201 as label 201 lies atop vacuum platen top 270. The vacuum is applied to enable label folding or reducing tool 210 to acquired label 201 before folding, or otherwise reducing the size of, label 201. The vacuum also provides tension to label 201 during the folding operation to help ensure that label 201 is maintained at a precise position above label folding tool 210 during the folding operation. Label hold down wheels 269 hold label 201 against the vacuum holes 271 in vacuum platen top 270 that are nearest label folding tool 210. Label hold down wheels 269 provide further support in maintaining the correct position of label 201 as it is passed along vacuum platen top 270 and during the folding operation.

A transfer adhesive is applied to label 201 to maintain label 201 in a folded orientation. The transfer adhesive is applied to label 201 using transfer adhesive dispenser ("TAD") 246. TAD 246 includes, for example: transfer adhesive pneumatic cylinder 247; tape dispenser back plate 248; tape apply tool 250; tape let out 252; encoder idler 255; and tape take out 254. Tape let out 252 is a hub on which a roll of transfer adhesive web is placed. Tape let out 252 includes idler 253, brake bar 259, and tape let out retainer 261. A full spool of a roll of transfer adhesive tape is secured onto tape dispenser back plate 248 using tape let out retainer 261. Tape take out 254 is a take-up hub for the transfer adhesive web as it is being used. Tape take out 254 includes transfer adhesive servo drive 257 and tape take out retainer 263. A take up spool for a discarded transfer adhesive backing is secured onto tape dispenser back plate 248 using tape take out retainer 263.

The transfer adhesive web is placed over first idler wheel 253, which is attached to brake bar 259. As the web is dispensed from the roll, first idler 253 is moved slightly due to tape tension, which releases brake bar 259, thus allowing the spool of web to unwind. Upon receiving a control signal from an ALS controller (not shown) transfer adhesive servo drive 257 advances the take up roll on tape take out retainer 263, thereby pulling the web from the feed spool. As the transfer adhesive web is dispensed, the web is passed over encoder idler 255 and then under tape apply tool 250. The discarded backing of the web is finally taken up onto the take up spool on tape take out retainer 263. Encoder idler 255 is connected to an encoder (not shown). The encoder measures how much tape as been dispensed, for example, approximately 0.5 inches of tape is dispensed per label. The encoder sends a signal to the ALS controller that the appropriate amount of tape has been dispensed, and the ALS controller in turns commands transfer adhesive servo drive 257 to, for example, stop.

The transfer adhesive is applied to label 201, for example, during the label folding/reducing operation. In alternative embodiments, the transfer adhesive may be applied to label 201 prior to or after the label reducing/folding operation. Label folding tool 210 is rotated several degrees, thus wrapping, or otherwise reducing the size of, label 201, until the desired location on label 201 for the transfer adhesive is substantially directly under tape apply tool 250. Tape dispenser back plate 248 pivots at pivot point 249, thus lowering tape apply tool 250 against label 201. Tape dispenser back plate 248 is rotated using pneumatic cylinder 247. The pivoting motion presses a portion of the transfer adhesive to label 201. The pneumatic cylinder 247 is then retracted to pull the web of transfer adhesive away from label 201. The web is threaded past, for example, an optional rubber foot (not shown) that is used to press the web against label 201 such that the transfer adhesive resides completely within the confines of label 201. The rubber foot provides a cushion and prevents label 201 from being damaged. The dimensions of the rubber foot, for example, ½ inch by ⅝ inch, optionally determines the area on label 201 that is covered with the transfer adhesive.

In an alternate embodiment, the transfer adhesive may be applied such that a portion of the transfer adhesive overhangs an edge of label 201. In this situation, only a portion of the transfer adhesive that resides on the surface of label 201 is used to maintain label 201 in a folded orientation. The overhanging portion of the transfer adhesive may be wrapped such that is connects with an outer side of folded label 201. This overhanging portion may be used to adhere label 201 to the medication container and, thus, obviates the use of any additional adhesive, such as a hot melt adhesive as described below, to affix label 201 to the medication container.

Vacuum, which is applied through, for example, vacuum holes 271 in vacuum platen top 270, holds label 201 in place as tape apply tool 250 is raised to pull the transfer adhesive from its backing on the transfer adhesive web. Once the backing is removed, vacuum platen top 270 continues to hold label 201 in place and to provide tension as the remainder of label 201 is folded onto label folding tool 210, as described below in greater detail.

Figure 8:
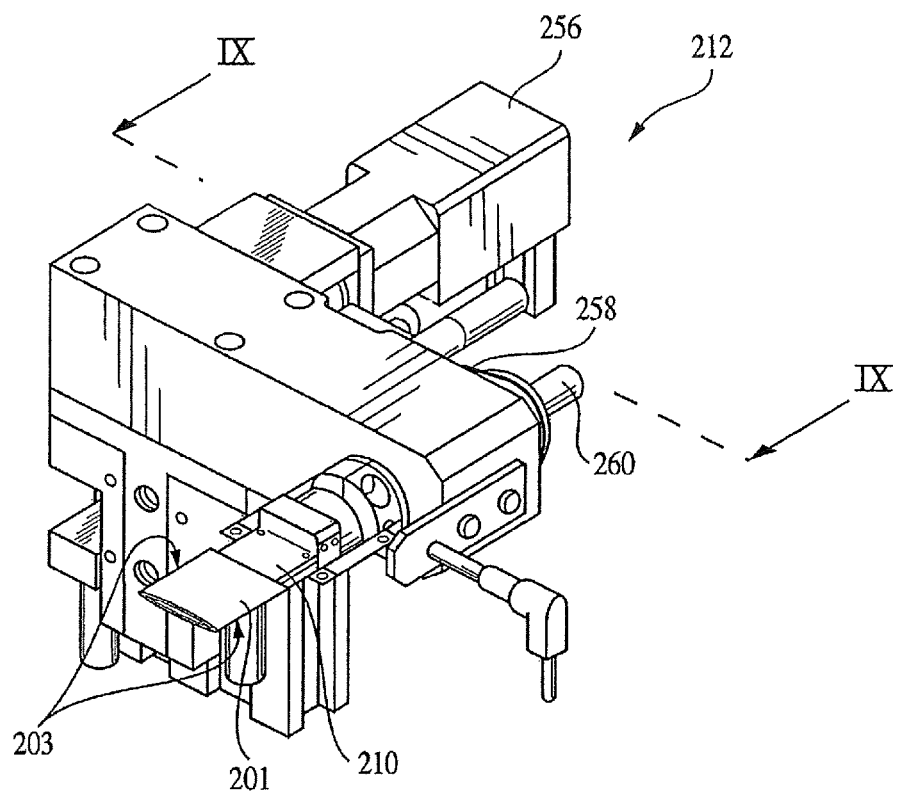
FIG. 8 illustrates a label-reducing tool of the present invention.
Figure 9:
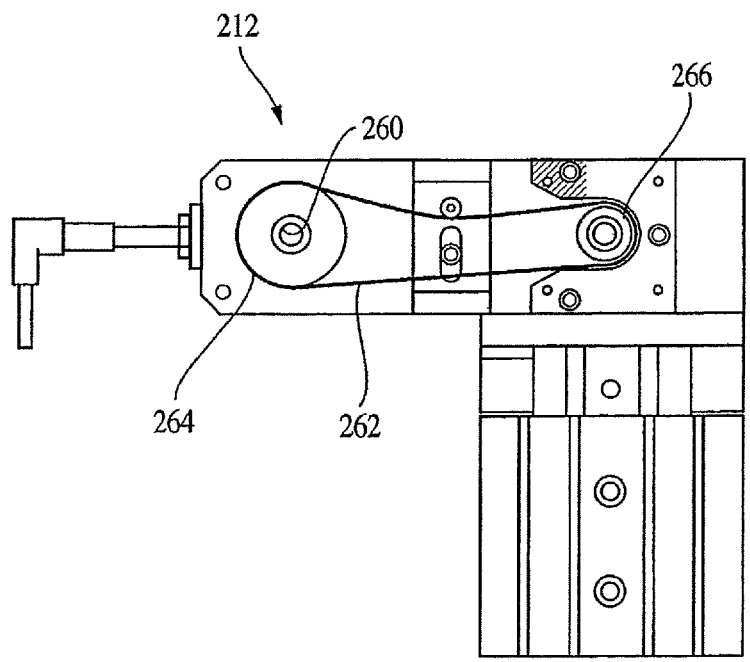
FIG. 9 illustrates a side view of the label-reducing tool of the present invention.

FIG. 8 illustrates a more detailed view of label folding tool 210 and spindle drive assembly 212. Spindle drive assembly 212 includes, for example: spindle drive servo 256 and spindle block 258. Label folding tool 210 is connected through spindle block 258 using label folding tool shaft 260. FIG. 9 illustrates a side, cut-away view of spindle drive assembly 212. Timing belt 262 is connected to spindle drive servo 256 using first timing belt pulley 266, which is, for example, a 32-teeth pulley. Timing belt 262 is also connected to label folding tool shaft 260 using second timing belt pulley 264, which is, for example, a 60-teeth pulley. Spindle servo drive 256 drives first timing belt pulley 266, which causes timing belt 262 to move. Timing belt 262 in turn drives second timing belt pulley 264, which causes label folding tool shaft 260 to rotate, thus allowing label folding tool 210 to rotate. In one embodiment, label 201 wraps around label folding tool 210 during the folding operation. Other standard label reducing operations may alternatively be used.

Figure 7:
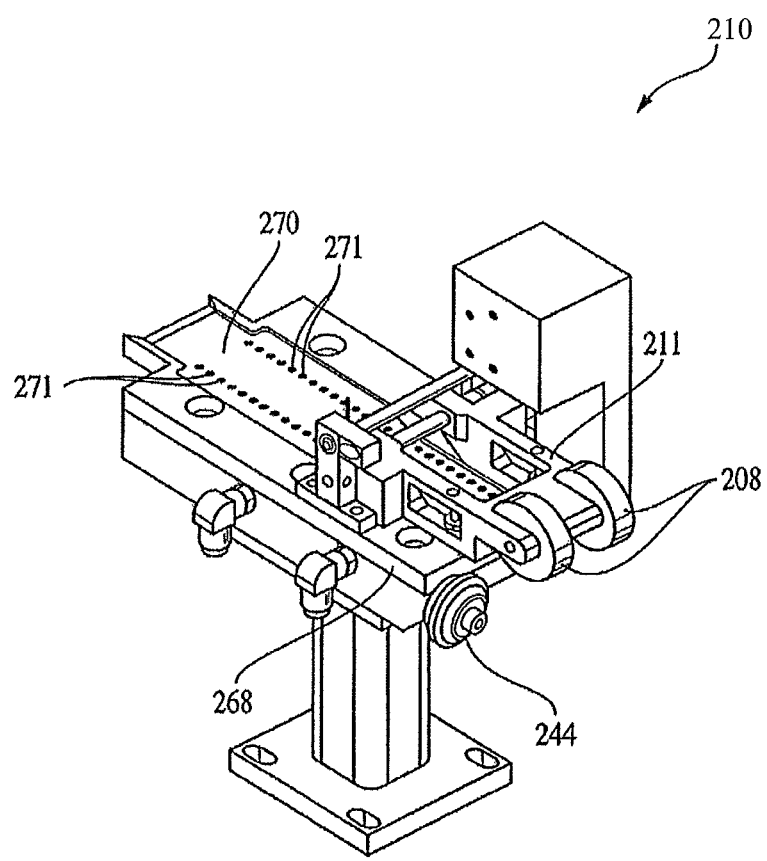
FIG. 7 illustrates an apparatus for creasing a label according to the present invention.

During the folding operation, first label creasing wheels 208 are positioned to abut against label folding tool 210. Label 201 passes between label folding tool 210 and first label creasing wheels 208 as label folding tool 210 rotates, causing label 201 to crease along fold edges 203 (see FIG. 8). First label creasing wheels 208 also apply pressure to label 201 to cause the transfer adhesive to stick and thus maintain label 201 in a folded orientation. As illustrated in FIG. 3A, first label creasing wheels 208 are held in position by creasing wheel support 209, which is mounted on main plate assembly 240. FIG. 7 illustrates an alternative embodiment in which first label creasing wheels 208 are held in position by creasing wheel support 211. In this embodiment, creasing wheel support 211 is mounted directly onto VPA upper guide 268.

Figure 10:
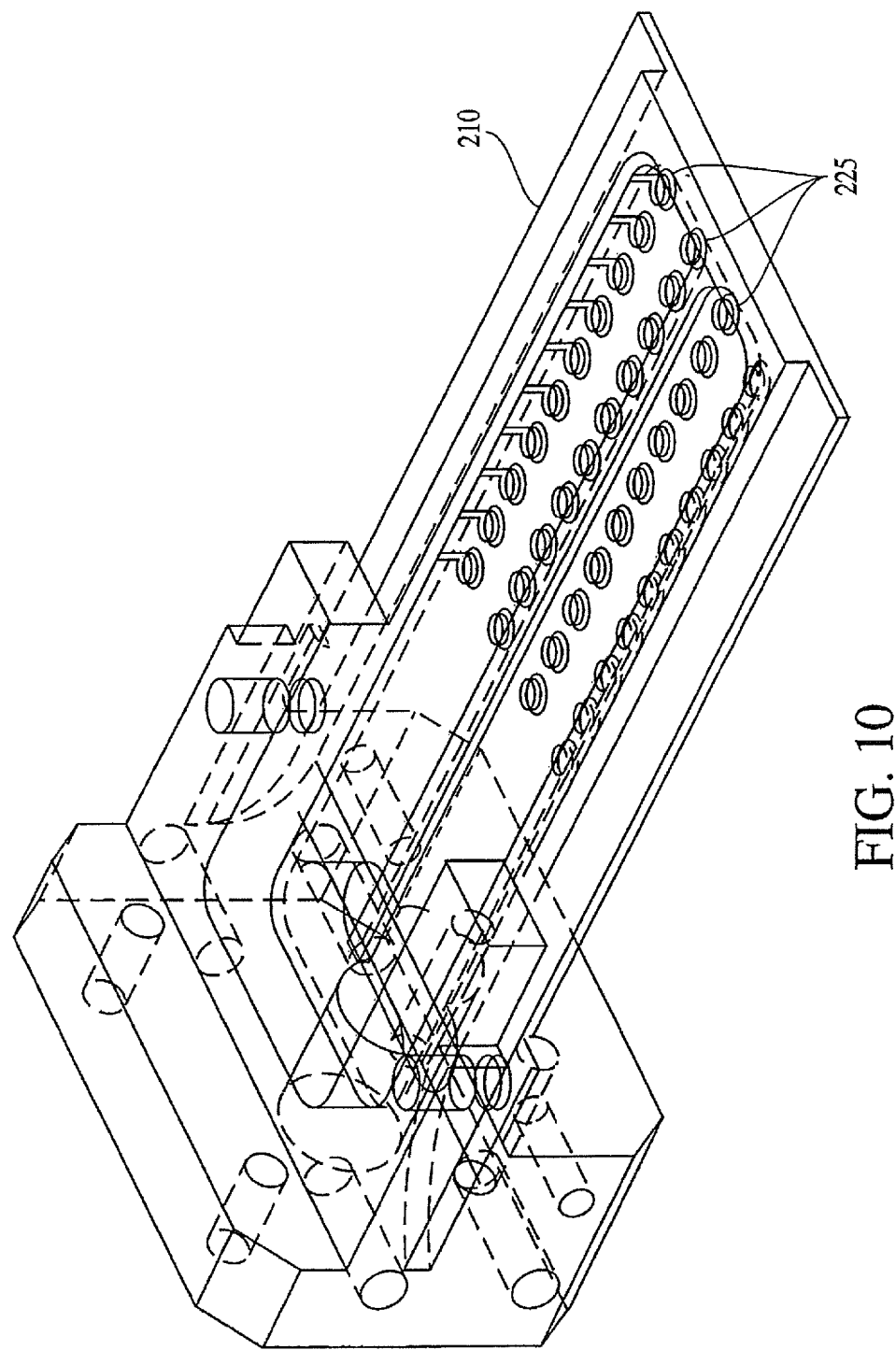
FIG. 10 illustrates a label folding tool according to the present invention.

FIG. 10 illustrates label folding tool 210 in greater detail. Label folding tool 210 has a plurality of vacuum holes 225. Vacuum holes 225 secure label 201 to label folding tool 210. When label 201 is fed out of printer 202, vacuum is applied through both vacuum holes 271 in vacuum platen top 270 and vacuum holes 225 in label folding tool 210. Vacuum platen top 270 is divided into two chambers, such that one chamber contains a group of holes, for example, half of vacuum holes 271, further from label folding tool 210, i.e., closer to printer 202, and the second chamber contains a group of holes near to label folding tool 210. Different arrangements of such chambers, of course, are possible. Vacuum applied through the group of vacuum holes 271 further from label folding tool 210 are used to secure label 201 to the surface of vacuum platen top 270 during, for example, application of the transfer adhesive to label 201. Once the transfer adhesive is applied, the vacuum applied through this further group of vacuum holes 271 is released.

In an alternate embodiment, the transfer adhesive is not applied such that label 201 is capable of being unrolled from the folded orientation, allowing a patient or consumer to view any information that may be printed on a surface of label 201 that is obscured by the folded orientation.

In another alternate embodiment, instead of label 210 being folded by label folding tool 210, a conventional machine may be used to fold label 201 such that label 201 is manipulated into a flag orientation, thus reducing the size of label 201. In this flag orientation, label 201 may be affixed to the medication container at one or both ends of label 201, as described below in greater detail.

Figure 11:
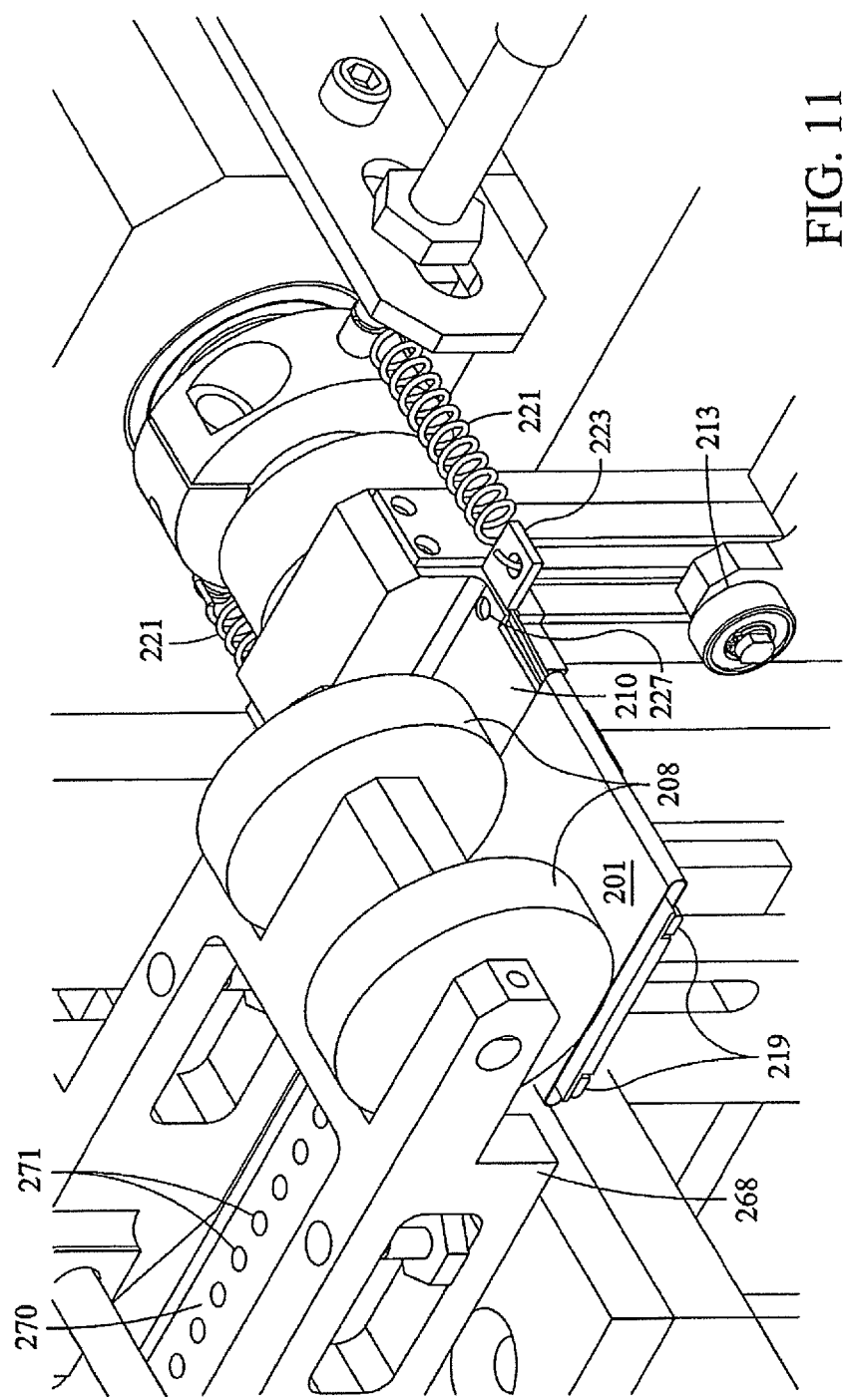
FIG. 11 illustrates a mechanism for stripping a label from a label folding tool according to the present invention.

After the folding operation is completed, label 201 is removed from label folding tool 210. FIG. 11 illustrates a mechanism by which label 201 may be stripped from label folding tool 210. Label folding tool 210 has label tension release fingers 219. Label tension release fingers 219 are alternately held in an open and a closed position by tension release finger springs 221 and label release cam followers 213.

While label 201 is on label folding tool 210, label tension release fingers 219 take up any slack in label 201 and ensure that label 201 is tightly wound around label folding tool 210. Label tension release fingers 219 are held in the open position by tension release finger springs 221. Tension release finger springs 221 are connected to tension release finger release tabs 223. Springs 221, for example, are extension springs such that it requires force to make springs 221 extend. By retracting and, thus, applying pressure to release tabs 223, springs 221 cause release tabs 223 to move around pivot point 227 and to move label tension release fingers 219 in the open position.

Label folding tool 210 and spindle drive servo 256 are mounted on an air cylinder (not shown) that can raise and lower. Label folding tool 210 is raised to an up position when receiving label 210 from vacuum platen top 270 and during the folding operation. Once the folding operation is completed, label folding tool 210 is lowered, for example, approximately 1½ inches, thus coming into contact with label release cam followers 213. Label folding tool 210 may also optionally be rotated 180° to ensure that all of label 201 is wrapped around label folding tool 210. Cam followers 213 press against label tension release fingers 219 at a location behind label 201. This causes label tension release fingers 219 to move to the closed position and causes slack in label 201. In an alternative embodiment, an activation device, e.g., a cylinder, may be used to press against label tension release fingers 219.

Figure 12:
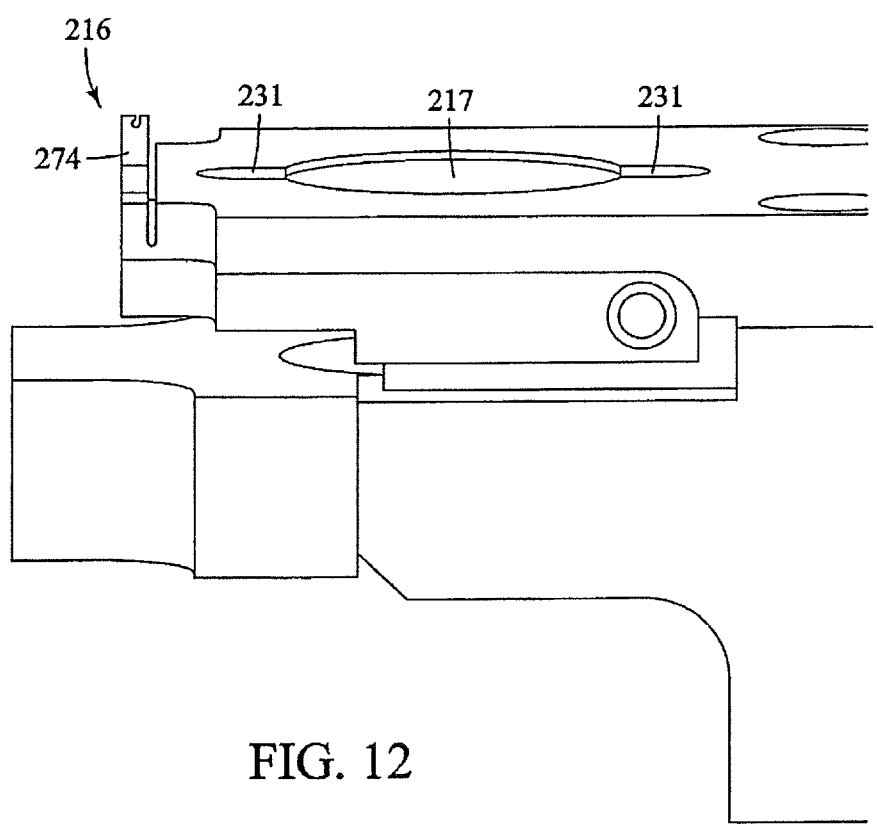
FIG. 12 illustrates a spring-loaded shuttle block according to the present invention.

Label 201 is removed from label folding tool 210 by shuttle block 216. FIG. 12 illustrates shuttle block 216 in greater detail. Shuttle block 216 includes, for example: vacuum pad 217; label reject perforator pin receptors 231; and spring-loaded ridge 274. Label folding tool 210 is lowered onto shuttle block 216 by the air cylinder after the folding operation is completed. Vacuum pad 217 employs a vacuum to hold label 201 in place on the surface of shuttle block 216 while removing label 201 from label folding tool 210 and while shuttle block 216 is in transit, as described below in greater detail.

Spring-loaded ridge 274 is pushed against the underside of label folding tool 210, with a back edge of label 201 being just inside of spring-loaded ridge 274. A settable cylinder stop (not show) optionally is used to limit downward movement of label folding tool 210 so that label folding tool 210 does not press label 201 too firmly against shuttle block 216. Vacuum is drawn on vacuum pad 217, securing label 210 to the surface of shuttle block 216. As shuttle block 216 begins to move, spring-loaded ridge pulls label 201 off of label folding tool 210, aided by the vacuum being applied to vacuum pad 217.

After being removed from label folding tool 210, label 201 is transported from label folding tool 210 by shuttle block 216 on shuttle block track 214. As seen in FIG. 3A, shuttle block 216 travels horizontally along shuttle block track 214 from label folding tool 210 to label reject mechanism 218. Igus chain 215 has a hollow interior inside which a vacuum line and sensor lines (not shown) leading to shuttle block 216 are contained during movement of shuttle block 216. Igus chain 215 attaches to shuttle block 216 at a first end and attaches to a stationary location at a second end, for example, spindle block 242. The second end slides back and forth along the stationary location while remaining affixed to shuttle block 216 at the first end.

After shuttle block 216 collects label 201 from label folding tool 210, it passes under an optional second label creasing wheel 244. Second label creasing wheel 244, which is, for example, a part of VPA 206, further creases edges 203 of label 201 as label 201 passes beneath second label creasing wheel 244. Second label creasing wheel 244 may be used in a pair, although only one is illustrated in FIG. 3A, such that one wheel creases each side of label 201. Furthermore, second label creasing wheel 244 may be located at any point along shuttle block track 214, for example, mid-way between label folding tool 210 and a hot melt glue application apparatus. A ski, or pair of skis in the case of two second creasing wheels, may be employed to guide label 201 beneath second label creasing wheel 244. Subsequent to the second creasing of label 201, at some further point along the traverse of shuttle block 216, hot melt glue is added to label 201, as will be described later in greater detail.

ALS 200 also enables label 201 to optionally be rejected before being affixed to a medication container. There are various reasons label 201 may be rejected. For example, label 201 may be rejected if the barcode printed on label 201 was not read by label scanner 204 after label 201 was printed, if label scanner 204 was unable to read the barcode printed on label 201, if label scanner 204 malfunctioned, if a medication container that is next in sequence to receive label 201 does not correspond to label 201 according to the barcode printed on label 201, etc. If label 201 is rejected before hot melt glue is applied to label 201, then label 201 is discarded using label reject mechanism 218 and rejected label assembly 220. Also, if label 201 is rejected after the hot melt glue has been applied or after label 201 has been affixed to the medication container, human intervention may be used to reject label 201.

Label reject mechanism 218 includes, for example: label reject perforator pins 230; label reject stripper plate 232; label reject vertical slide 236; and label reject horizontal slide 238. Rejected label assembly 220 includes, for example: label discard bin 222; right discard bin slide 224; left discard bin slide 226; and rejected label drop tube 234. Right discard bin slide 224 and left discard bin slide 226 allow removal of label discard bin 222 from rejected label assembly 220.

If label 201 is rejected, label reject mechanism 218 is positioned over shuttle block 216 using label reject horizontal slide 238. Label reject mechanism 218, including, label reject stripper plate 232 and label reject perforator pins 230, is then lowered over label 201 using label reject vertical slide 236. Label stripper plate 232 has holes 233 to accommodate label reject perforator pins 230. Label stripper plate is oriented such that label reject perforator pins 230 must pass through holes 233 to reach label 201. Label reject stripper plate 232 holds label 201 in place on vacuum pad 217, which is on shuttle pad 216. Label reject perforator pins 230 are advanced through label 201 and into label reject perforator pin receptors 231 located adjacent to vacuum pad 217. Label reject perforator pins 230 are optionally ridged to prevent label 201 from slipping off. Once label reject perforator pins 230 are extended through label 201, the vacuum on vacuum pad 217 is released and both label reject perforator pins 230 and label reject stripper plate 232 are raised.

Label reject mechanism 218 is positioned over rejected label drop tube 234 using label reject horizontal slide 238. A combination of movements of label reject mechanism 218 and rejected label drop tube 234 is also possible. Label reject stripper plate 232 is then lowered past label reject perforator pins 230 to remove label 201 from label reject perforator pins 230. Label 201 falls through rejected label drop tube opening 235 and passes though rejected label drop tube 234 into label discard bin 222. At the bottom of rejected label drop tube 234, an optional photocell array (not shown) advantageously detects label 201 as it falls into label discard bin 222. The photocell array enables confirmation that label 201 has been successfully rejected, providing positive label accountability.

After label 201 is affixed to the medication container, the barcode printed on label 201 once again is optionally scanned by folded label scanner 228. This second scanning operation provides a further confirmation that label 201 is properly correlated with the medication particular for which label 201 is intended. In another embodiment, label 201 is optionally scanned a second time when shuttle block 216 reaches the opposite end of shuttle block track 214 before label 201 is affixed to the medication container.

In order to enable label 201 to be affixed to a package, hot melt glue is applied to label 201 using a standard hot melt glue application assembly. The hot melt glue may be applied to label 201 at any point on shuttle block's 216 traverse path between label folding tool 210 and label reject mechanism, such as at the end of the movement of shuttle block 216 along shuttle block track 214. Alternatively, the hot melt glue may be applied to label 201 after it has been determined that label 201 will not be rejected. The hot melt glue application assembly (not all parts of which are shown) includes a glue gun, a heated tank that contains the hot melt glue in liquid form, a heated hose that enables passage of the hot melt glue from the heated tank to the glue gun, and a pump, which moves the hot melt glue through the heated hose. For example, a standard Nordson hot melt glue system may be used for the hot melt glue application assembly, in which the heated tank/pump is a Nordson Model 3400 and the glue gun is a Nordson Model H-200 pneumatic gun.

Figure 13A:
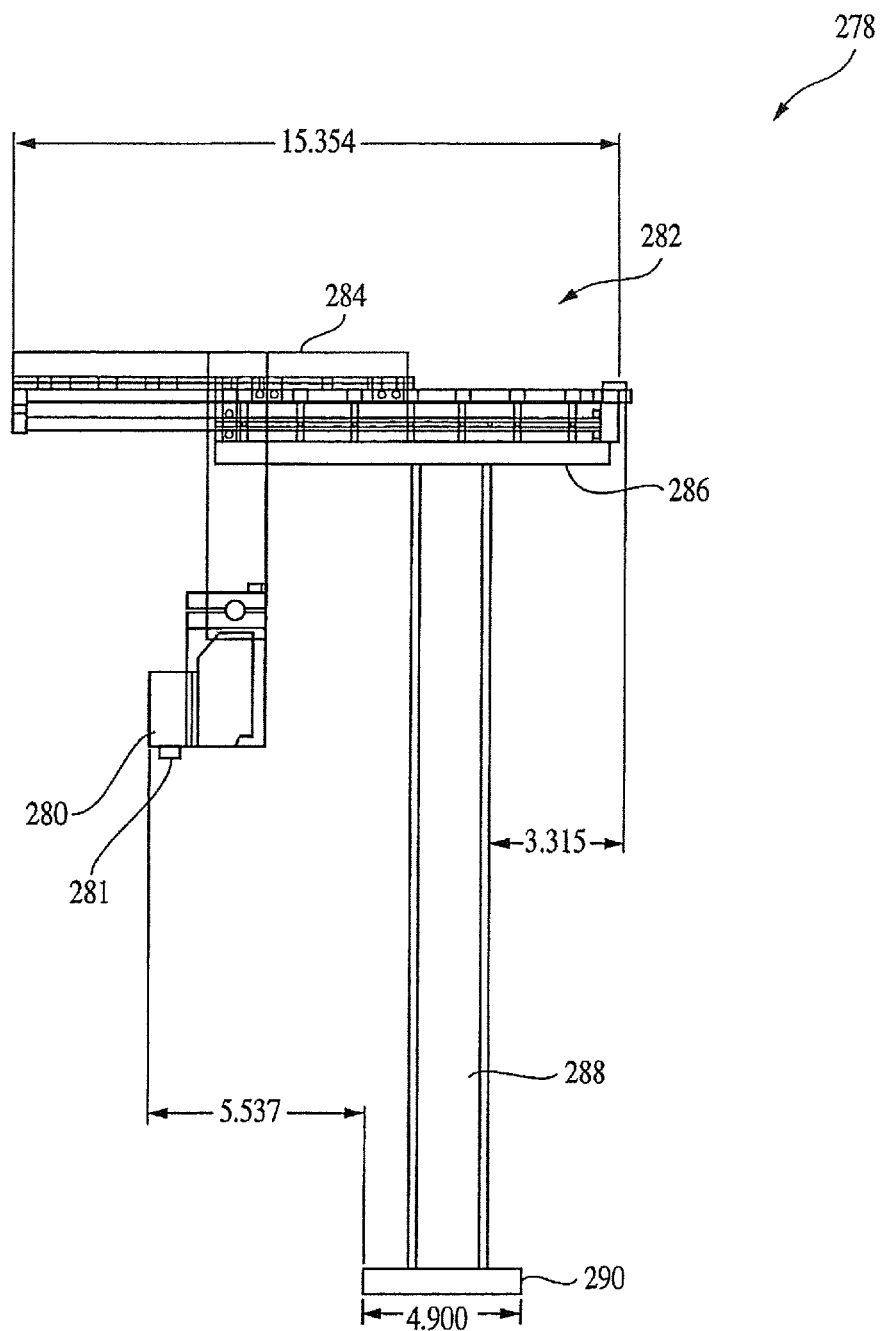
FIGS. 13A, 13B, and 13C illustrate a hot melt glue gun.

FIG. 13A illustrates hot melt glue gun assembly, denoted generally by reference numeral 278. Hot melt glue gun assembly 278 includes, for example: hot melt glue gun 280 with nozzle 281; glue gun slide assembly 282; glue gun support 288; and glue gun base 290. Hot melt glue gun assembly 278 also includes a standard hot melt glue controller (not shown) that regulates the timing of hot melt glue gun 280. The system PLC controller controls the positioning of glue gun slide assembly 282. Nozzle 281 may be, for example, a five-hole nozzle to enable simultaneous distribution of a plurality of glue dots to label 201, as will be discussed later in greater detail.

Glue gun slide assembly 282 includes, for example: mobile glue gun slide 284 and stationary glue gun slide 286. Slide assembly 282 may use pneumatics to enable mobile glue gun slide 284 to move relative to stationary glue gun slide 286. As may be seen in FIG. 13B, which is a side view of hot melt glue gun assembly 278, hot melt glue gun 280 may be offset from glue gun support 288. FIG. 13C illustrates the optional five-hole nozzle design of nozzle 281. Note that four holes 292 are shown and that a fifth hole 292 is obscured by the isometric view of FIG. 13C. The hot melt adhesive is expelled through holes 292 onto label 201. Connector 294 links nozzle 281 to the remainder of hot melt glue gun 280. Of course, alternate glue nozzles and/or other types of standard hot melt applicators may be used to deliver different glue patterns.

Hot melt glue gun assembly 278 may be placed adjacent to ALS 200 such that hot melt glue gun 280 is positioned over shuttle block track 214. As mentioned previously, hot melt glue gun assembly 278 may be positioned at any location along shuttle block track 214 between label folding tool 210 and label reject mechanism 218. Alternatively, hot melt glue gun assembly 278 may be positioned contiguous with label reject mechanism 218 such that label reject mechanism 218 and hot melt glue gun 280 operate at substantially the same location along shuttle block track 214. The hot melt glue typically has a limited usable time until the glue cures during which the glue retains sufficient liquidity to be usable as adhesive. If a label to which the hot melt glue has been applied is not affixed to the container during this time, the label is rejected.

Glue gun slide assembly 282 enables hot melt glue gun 280 to move at some angle to shuttle block track 214. The angle may be parallel to shuttle block track 214, such that glue gun slide assembly controls positioning of hot melt glue gun 280 and nozzle 281 over label 201 in one dimension, for example, a x-direction. In this situation, positioning in a y-direction of the label under hot glue gun 280 and nozzle 281 is controlled by shuttle block 216. Alternative orientations of hot melt glue gun assembly 278 may be used that would enable application of the hot melt adhesive to label 201. Other elements of the hot melt glue application assembly, i.e., the controller, the heated tank, the heated hose, and the pump may optionally be located at a location remote from ALS 200. The location of the other elements is limited only by the length of the heated hose that is employed to connect the heated tank and hot melt glue gun 280.

As described previously, if label 201 is rejected after the hot melt glue is applied to label 201, a human operator may remove label 201 from shuttle block 216, rather than label reject mechanism 218 being employed. This prevents the hot melt glue from getting on any of the parts of label reject mechanism 218. Label accountability still is achieved even if such human intervention, is utilized.

Figure 14:
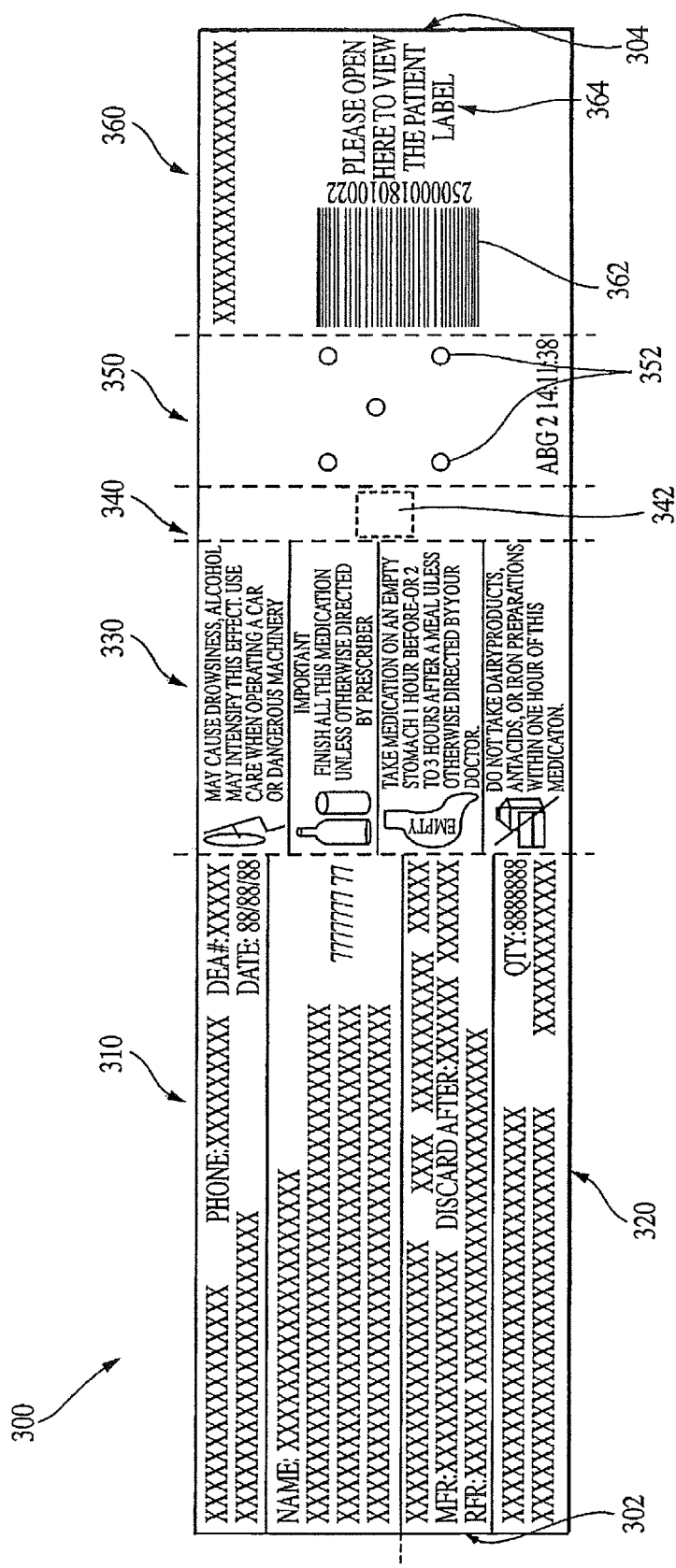
FIG. 14 illustrates a label according to the present invention.

FIG. 14 illustrates a patient label to be used with ALS 200, denoted generally by reference numeral 300. Note: the patient label depicted in FIG. 14 (and FIG. 15) is not to scale. Patient label 300 is formed, for example, from a white, smooth, high gloss, paper stock designed for use in thermal transfer ribbon printers or other standard printers. Information is printed on patient label 300 by printer 202 (see FIG. 3B). Patient label 300 is defined by a first end 302 and a second end 304, where a length of patient label 300 is defined by, or extends between, first end 302 and second end 304. Patient label 300 is preferably between 11 inches and 12 inches in length and between 1.25 inches and 1.75 inches in width. Alternative label sizes may also be used. The width of patient label 300 is determined by the width of the paper stock and the length is achieved by paper stock cutting means (not shown) located in printer 202. The length to which label 201 is cut may be a pre-set value in printer 202.

Patient label 300 contains a plurality of information pertaining to a patient and to the medication contained in the container to which patient label 300 is to be affixed. Patient label 300 includes, for example: customer information section 310; medication information section 320; use instruction section 330 indicating correct usage of the medication; label securing section 340; surface securing section 350; and barcode section 360.

Customer information section 310 contains, for example, the patient's name, the patient's address and phone number, the name of the patient's physician, the physician's phone number, and/or particular dosage directions for the patient. Medication information section 320 contains, for example, the name of the medication, the strength of the prescription, the amount of medication, the expiration date of the medication, and/or an indication of whether and how many refills are allowed. Use instruction section 330 contains, for example, any particular instructions regarding use of the medication. For instance, information such as "Shake Well Before Use" and "Take On An Empty Stomach" may be included in use instruction section 330.

Label securing section 340 defines a location on patient label 300 at which a transfer adhesive 342 is applied. When folded, label securing section 340 is secured to an adjacent face of patient label 300, thus enabling patient label 300 to be held in the folded, or otherwise reduced, orientation. Transfer adhesive 342 adheres to, for example, the underside of barcode section 360, where the underside is the side of patient label opposite the side that contains the printed information. Label securing section 340 is preferably between 0.75 inch and 1 inch in length and between 1.25 inches and 1.75 inches in width, where the dimensions of length and width are defined by, or result from, patient label 300. Other sizes of label securing section 340 may be used. It should be noted that the width of label securing section 340 is limited by the width of patient label 300.

The consistency of transfer adhesive 342 is preferably such that the transfer adhesive applies cleanly to patient label 300 without residual strings of adhesive remaining between patient label 300 and the disposable backing. The transfer adhesive is, for example, a standard Hi-Tact Acrylic 3M adhesive or an equivalent. Furthermore, the transfer adhesive allows patient label 300 to be unfolded and refolded without damaging patient label 300.

Surface securing section 350 defines a location on patient label 300 at which hot melt adhesive 352 is applied. When folded, surface securing section 350 is disposed on an outward face of patent label 300, thus enabling patient label 300 to be affixed to a container containing the appropriate medication corresponding to patient label 300. Surface securing section 350 is preferably between 1.5 inches and 1.75 inches in length and between 1.25 inches and 1.75 inches in width, where the dimensions of length and width are defined by, or result from, patient label 300. Other sizes of surface securing section 350 may be used. It should be noted that the width of surface securing section 350 is limited by the width of patient label 300. Hot melt adhesive 352 is preferably a medium viscosity pressure sensitive hot melt adhesive that exhibits a strong tack and give a permanent bond, for example, a rubber-based adhesive.

Figure 13B:
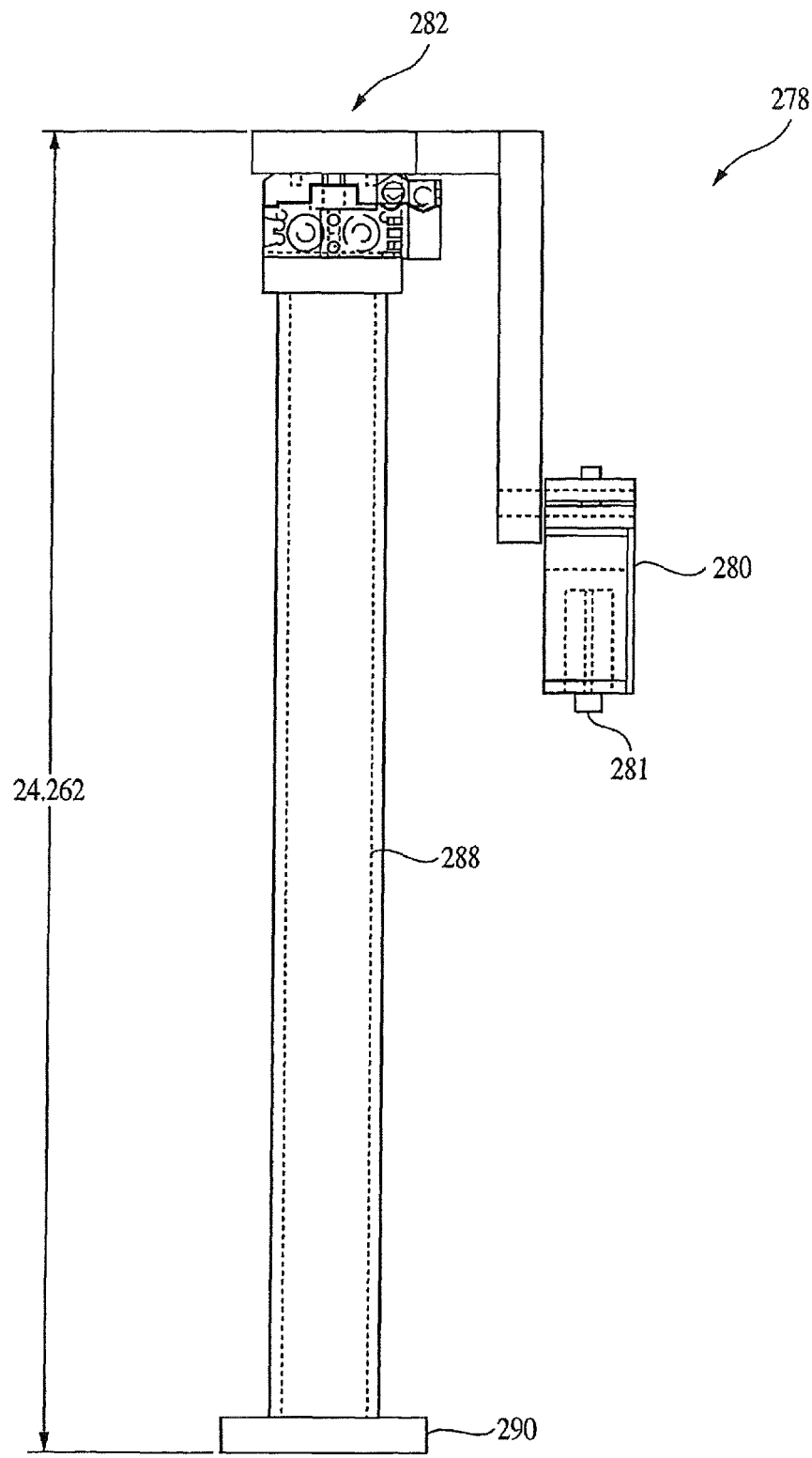
Figure 13C:
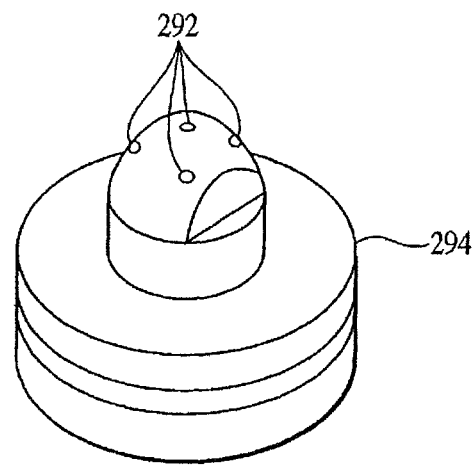
Figure 15A:
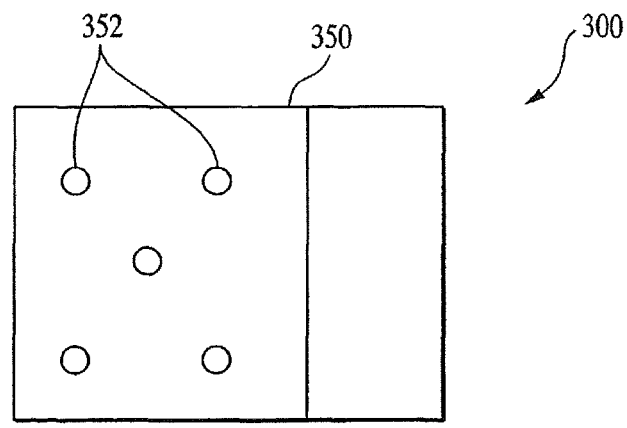
FIGS. 15A, 15B, and 15C illustrate various distributions of hot melt adhesive according to the present invention.
Figure 15B:
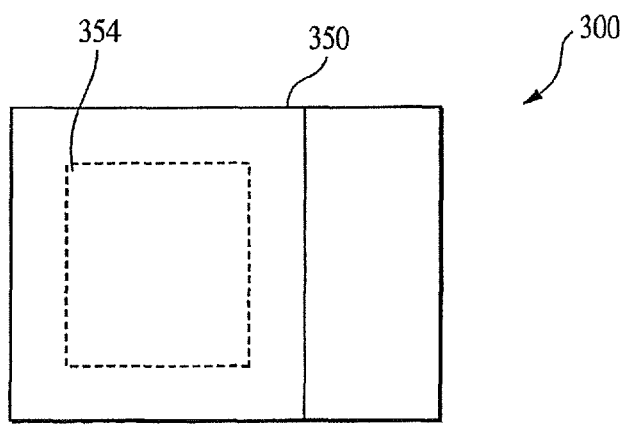

FIGS. 13A and 13B illustrate alternative embodiments for the distribution of hot melt adhesive 352 in surface adhesive securing section 350. In FIG. 15A, hot melt adhesive 352 is distributed in a five-dot pattern. This five-dot pattern is applied, for example, using nozzle 281, where nozzle 281 is a five-hole nozzle. Although a five-dot pattern is illustrated, it should be appreciated that a variety of glue-dot patterns are possible. In an alternate embodiment, a different nozzle 281, such as a single-hole nozzle, may apply the five-dot pattern. Swirl nozzles may also be used to apply the desired pattern. In this situation, the five-dot pattern is applied by coordinating the movement of shuttle block 216 along shuttle block track 214 and glue gun slide assembly 282 to move patient label 300 and hot melt glue gun 280 in the appropriate manner to create the five-dot pattern. In another alternate embodiment, as seen in FIG. 15B, hot melt adhesive 352' may be applied in a continuous section rather than in discrete locations.

Alternatively, in another embodiment, the hot melt adhesive, or optionally, some other type of adhesive, may be placed on patient label 300 prior to the folding/reducing operation, such as in the case of a self-adhesive label. In this situation, a separate hot melt adhesive, as described with reference to hot melt assembly 278, may or may not be applied to patient label 300. An optional adhesive protector may then subsequently be removed after the label is folded/reduced to thereby expose the adhesive that was pre-affixed to the label, for example, from the factory providing the label.

Figure 15C:
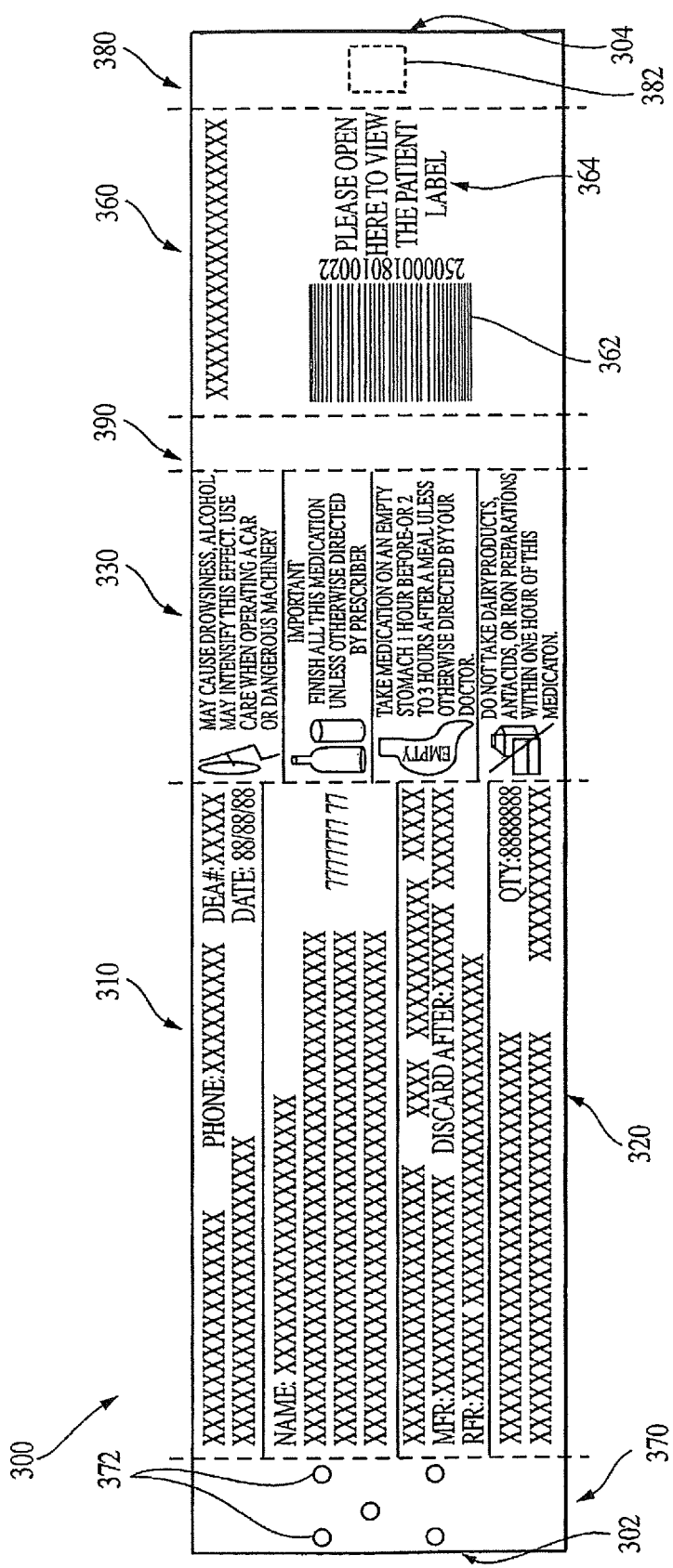

FIG. 15C illustrates a possible distribution of hot melt adhesive 352 when patient label 300 is in a flag orientation, as discussed previously. In this embodiment, patient label 300 alternately includes first surface securing adhesive section 370 and second surface securing adhesive section 380. First securing adhesive section 370 contains first hot melt adhesive 372 and second surface securing adhesive section 380 contains second hot melt adhesive section 382 at first end 302 and second end 304, respectively. First hot melt adhesive 372 and second hot melt adhesive 382 may be applied in a variety of configurations, as discussed with reference to FIGS. 15A and 15B.

First hot melt adhesive 372 and second hot melt adhesive 382 may be in identical configurations or in different configurations, as illustrated in FIG. 15C. Also, label securing adhesive section 340 and surface securing adhesive section 350 are omitted in this embodiment, although the space in which label securing adhesive section 340 and surface securing adhesive section 350 were oriented may be retained on patient label 300, as illustrated by space 390. In this embodiment, patient label 300 is secured to the medication container at first surface securing adhesive section 370 and second surface securing adhesive section 380 to form a flag that protrudes from the medication container.

Barcode section 360 contains, for example, an item barcode 362. Item barcode 362 corresponds to a product barcode on the medication and/or medication container to which patient label 300 is to be affixed. As described previously, a database stores information identifying the medication containers, using the product bar code as a reference, and their appropriate labels. By scanning item barcode 362 and the barcode on the medication container and determining whether the barcodes correspond, the system PLC of ALS 200 can determine whether or not a particular patient label 300 is the appropriate label for that medication. For example, the system PLC may check to ensure that medication container and the label affixed to that container both have the correct product barcode and item barcode 362, respectively.

Barcode section 364 may also contain opening instructions 364, which indicate to the consumer how to release patient label 300 from its secured, folded orientation such that the consumer can view all of the information printed on patient label 300. Furthermore, barcode section 364 may include other indicia, for example, a name of the medication contained in the medication container, thus enabling easy identification of the medication even while patient label 300 is folded. An example of further details regarding the information that may be printed on patient label 300 may be found in APPENDIX A.

Figure 16:
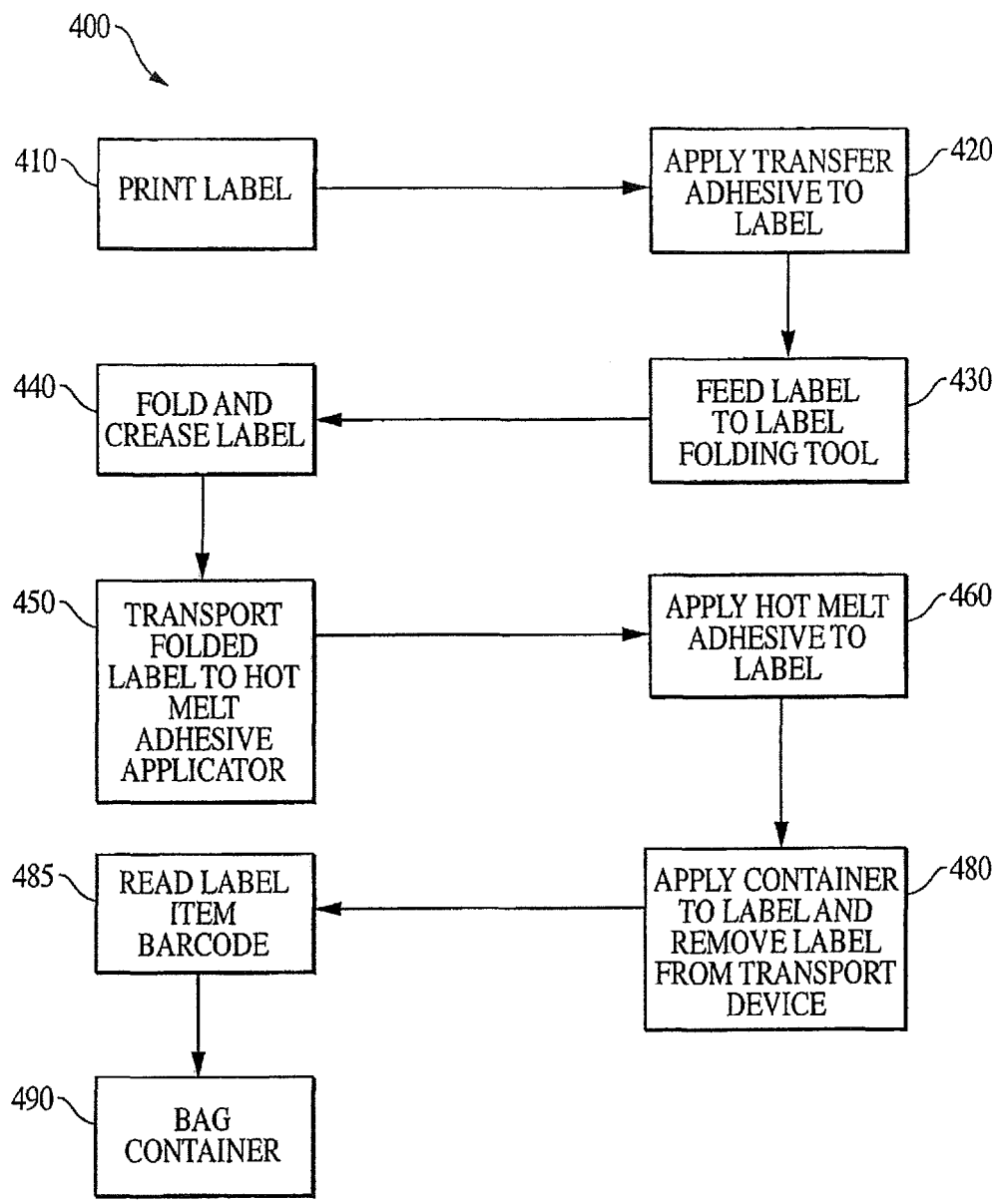
FIG. 16 is a flow chart illustrating a method for automated labeling of a medication container according to the present invention.

FIG. 16 illustrates a flow chart of a method for operation of ALS 200, denoted generally by reference numeral 400. ALS method 400 begins when printer 202 prints patient label 300, step 410. Transfer adhesive dispenser 246 then applies the transfer adhesive, for example, transfer adhesive 342, to label securing section 342 on patient label 300, step 420.

Patient label 300 is then fed to label folding tool 210, step 430. Patient label 300 is then rolled, or otherwise reduced, by label folding tool 210 and optionally creased by first label creasing wheels 208, step 440. Shuttle block 216 then transports the folded patient label 300, or alternately, the unfolded patient label 300, from label folding tool 210 to hot melt glue gun assembly 280, step 450. During transporting step 450, patient label 300 optionally is further creased by second label creasing wheel 244, provided that patient label 300 is in a folded, or otherwise reduced, orientation. Hot melt glue gun 280 applies the hot melt glue, for example, hot melt adhesive 352, to surface securing section 350 on patient label 300, step 460.

After the hot melt adhesive has been applied, a label application device applies the appropriate medication container to patient label 300 by pressing the medication container against the hot melt glue, step 480. The label application device includes, for example, a robotic arm and a controller. After applying the medication container to patient label 330, the label application device carries patient label 330 and the medication container to a label scanning location. In one embodiment, folded label scanner 228 may be placed at this label scanning location rather than along shuttle block track 214 (see FIG. 3A). The label scanning location may be above the bag into which patient label 300 and the medication container are placed subsequent to verification.

In applying patient label 300 to the appropriate medication container, in one embodiment the label application device, such as a robotic arm, retrieves the medication container and applies the medication container to surface securing section 350, or alternately, first surface securing section 370 and second securing section 380, of patient label 300 while patient label 300 is still resting on vacuum pad 217 of shuttle block 216. Vacuum pad 217 then removes the vacuum from patient label 300, allowing patient label 300 to be removed from shuttle block 216. As indicated above, the steps described herein (above and below) may be done sequentially, non-sequentially, or independent of each other so long as the overall functionality is performed as described herein.

Figure 17:
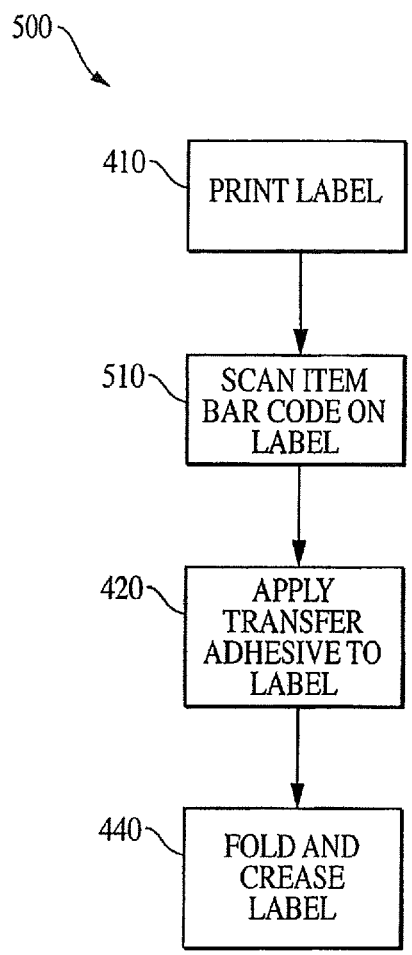
FIG. 17 is a flow chart illustrating a method for verifying a correlation between the label and a particular medication container.

FIG. 17 illustrates a flow chart further describing the operation of ALS 200, denoted generally by reference numeral 500. In ALS operation method 500, after printer 202 prints patient label 300, step 410, label scanner 204 scans item barcode 362 in barcode section 360 of patient label 300, step 510. Scanning item barcode 362, which corresponds to the product barcode on the medication and/or medication container to which patient label 300 is to be affixed, facilitates correct correlation of patient label 300 to the correct medication. Furthermore, scanning item barcode 362 ensures the print quality of label patient label 300. If, for example, elements of a print head in printer 202 burn out, generally, item barcode 362 will be unreadable by label scanner 204. The transfer adhesive is then applied to patient label 300, step 420, and patient label 300 is rolled and crease, step 440, as described in reference to FIG. 16.

Figure 18:
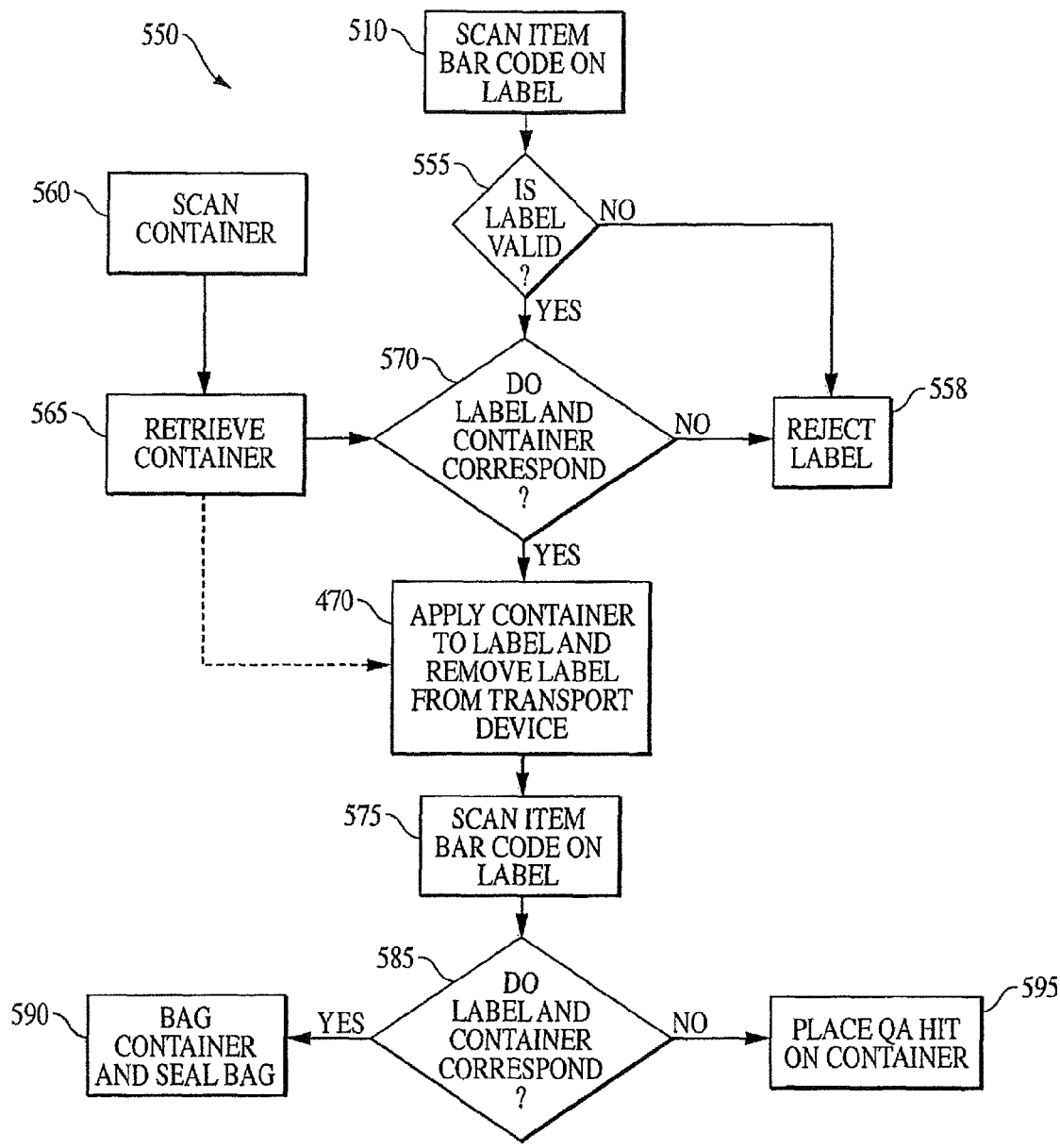
FIG. 18 is a flow chart illustrating a method for further verification of a correlation between the label and a particular medication container.

FIG. 18 illustrates a flow chart of a method for further verification of the correct correlation between patient label 300 and the medication to which patient label 300 is to be affixed, denoted generally by reference numeral 550. As described with respect to FIG. 17, label scanner 204 scans item barcode 362 on patient label 300, step 510. The system PLC determines whether or not patient label 300 is valid, step 555. Patient label 300 may be considered in valid if, for example, item barcode 362 was not read by label scanner 204, if label scanner 304 was unable to read item barcode 362 because of poor print quality or other such defect, if label scanner 204 malfunction, etc.

If patient label 300 is determined to be invalid, patient label 300 may be rejected, step 580. If patient label 300 is rejected before the hot melt adhesive is applied, patient label 300 may be rejected using label reject mechanism 218 and rejected label assembly 220, as described previously. If the hot melt adhesive has already been applied before the system PLC determines that patient label 300 is to be rejected, a human operator may intervene any physically remove patient label 300 from ALS 200.

A product scanner (not shown) independently scans the product barcode on the medication container in a scan tunnel, step 560. The scan of the product barcode may be performed before, after, or concurrently with the scan of item barcode 362. After the product barcode is scanned, the label application device retrieves the medication container and prepares the medication container for labeling, step 565.

If patient label 300 was determined to be valid at step 555, the system PLC may optionally determine whether the item barcode 362 on patient label 300 and the product barcode on the medication container correspond, step 570, as previously described. For example, the system PLC references the database to determine if the label information identified by item barcode 362 and the medication information identified by the product barcode correspond. If patient label 300 and the medication contained in the medication container do not correspond, patient label 300 may be rejected, step 580. Again, this rejection may be performed using label reject mechanism 218 and rejected label assembly 220 if patient label 300 is rejected before the hot melt adhesive is applied and by a human operator if the hot melt adhesive has already been applied to patient label 300.

If patient label 300 and the medication container do correspond, the label application device applies the medication container to patient label 300 and removes patient label 300 from shuttle block 210, step 470, as described previously. Folded label scanner 228 performs a second scan on item barcode 362, step 575. This second scan may occur at a scanning location remote from ALS 200, i.e., near the bag, itself, or alternately folded label scanner 228 may be situated at the end of shuttle block track 214, as seen in FIG. 3A.

The system PLC may then make a second verification of the correspondence of patient label 300 and the medication container, step 585. In an alternative embodiment, the verification by the system PLC at step 570 may be omitted, as indicated by the dashed arrow in the flowchart. In this situation, the verification at step 585 is the first verification of the correspondence of patient label 300 and the medication container. If patient label 300 and the medication container correspond, the medication container and attached patient label 300 are bagged and the bag is sealed, step 590.

If, however, patient label 300 and the medication container do not correspond, since patient label 300 is already affixed to the medication container, ALS 200 bags the medication container and affixed patient label. A quality assurance ("QA") error, or hit, is noted by the system PLC and the bag is not sealed. The QA hit causes the bagged medication container to be routed to a downstream Manual QA resolution station, where a human operator may resolve the issue. ALS 200 may pause if an error is detected, e.g., a label mismatch, folded label scanner 228 malfunctions, folded label scanner 228 cannot read item barcode 362, patient label 300 is missing, etc., and may require a human operator to restart the operation of ALS 200.

Figure 19:
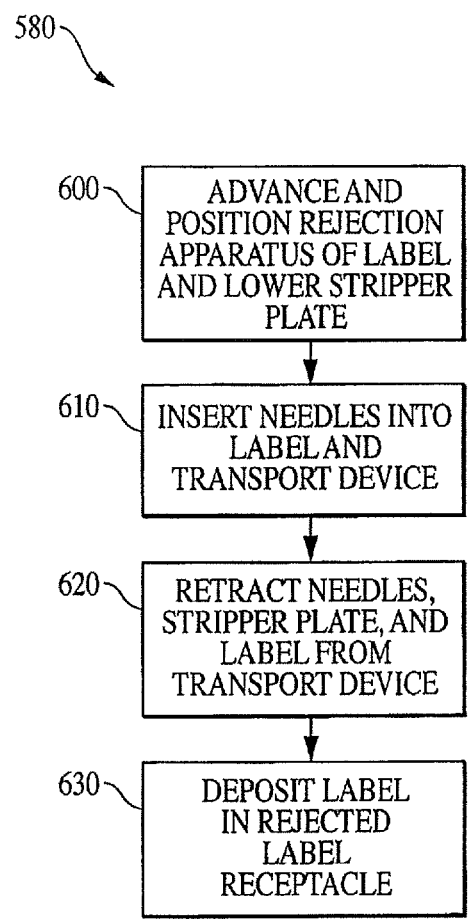
FIG. 19 is a flow chart illustrating a method for rejecting a defective label.

FIG. 19 illustrates a flow chart of a method of rejecting patient label 300, step 580 (see FIG. 18). Label reject method 580 begins as label reject mechanism 218, including label reject perforator pins 230 and label reject stripper plate 232, is advanced and positioned over patient label 300 as it rests on shuttle block 216, step 600. Label reject stripper plate 232 is lowered over patient label 300 to hold patient label 300 in place on shuttle block 216 and label reject perforator pins 230 are inserted into patient label 300, step 610. Shuttle block 216 has label reject perforator pin receptors 231 (see FIG. 12) to accommodate label reject perforator pins 230.

Vacuum pad 217 releases the vacuum on patient label 300 and label reject perforator pins 230 and label reject stripper plate 232 are then retracted, thus lifting patient label 300 from shuttle block 216, step 620. Label reject mechanism is then positioned over rejected label drop tube 234 and label reject perforator pins 230 are retracted from label reject stripper plate 232, thus causing patient label 300 to fall into rejected label drop tube opening 235, and to pass through rejected label drop tube 234 into label discard bin 222, step 630.

As discussed previously, it should be noted that label reject method 580 is used, for example, when patient label 300 is rejected before the hot melt adhesive is applied to patient label 300. If the hot melt adhesive is applied to patient label 300 before it is determined whether or not patient label 300 is to be rejected, then a human operator optionally removes patient label 300 from shuttle block 216. This is to prevent any of the hot melt adhesive from getting onto any of the parts of label reject mechanism 218, i.e., label reject perforator pins 230 and label reject stripper plate 232. The human operator may then dispose of the rejected patient label 300 into label discard bin 222.

Figure 20:
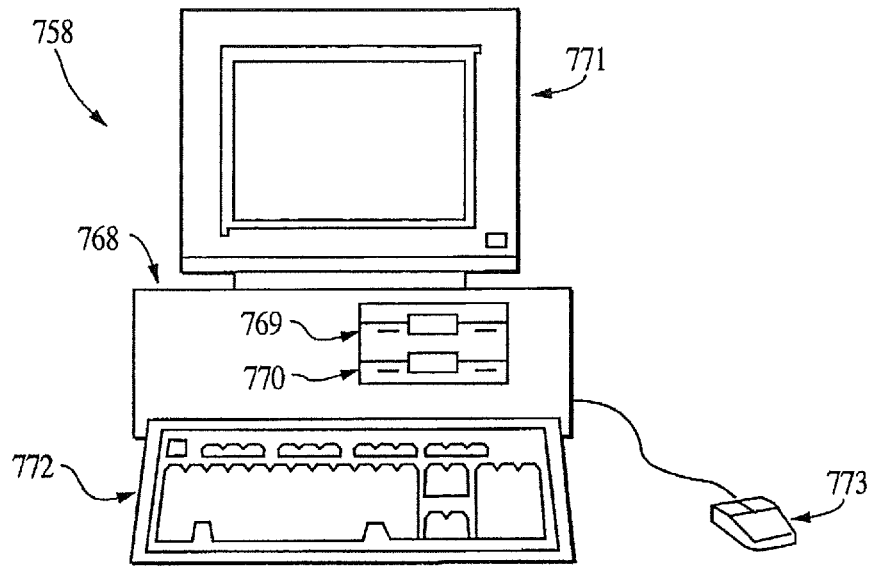
FIG. 20 is an illustration of a computer used for implementing the computer processing in accordance with a computer-implemented embodiment of the present invention.

FIG. 20 is an illustration of a computer 758 used for implementing the computer processing in accordance with a computer-implemented embodiment of the present invention. The procedures described above may be presented in terms of program procedures executed on, for example, a computer or network of computers.

Viewed externally in FIG. 20, computer 758 has a central processing unit (CPU) 768 having disk drives 769, 770. Disk drives 769, 770 are merely symbolic of a number of disk drives that might be accommodated by computer 758. Typically, these might be one or more of the following: a floppy disk drive 769, a hard disk drive (not shown), and a CD ROM or digital video disk, as indicated by the slot at 770. The number and type of drives varies, typically with different computer configurations. Disk drives 769, 770 are, in fact, options, and for space considerations, may be omitted from the computer system used in conjunction with the processes described herein.

Computer 758 also has a display 771 upon which information may be displayed. The display is optional for the computer used in conjunction with the system described herein. A keyboard 772 and/or a pointing device 773, such as a mouse, may be provided as input devices to interface with central processing unit 768. To increase input efficiency, keyboard 772 may be supplemented or replaced with a scanner, card reader, or other data input device. The pointing device 773 may be a mouse, touch pad control device, track ball device, or any other type of pointing device.

Figure 22:
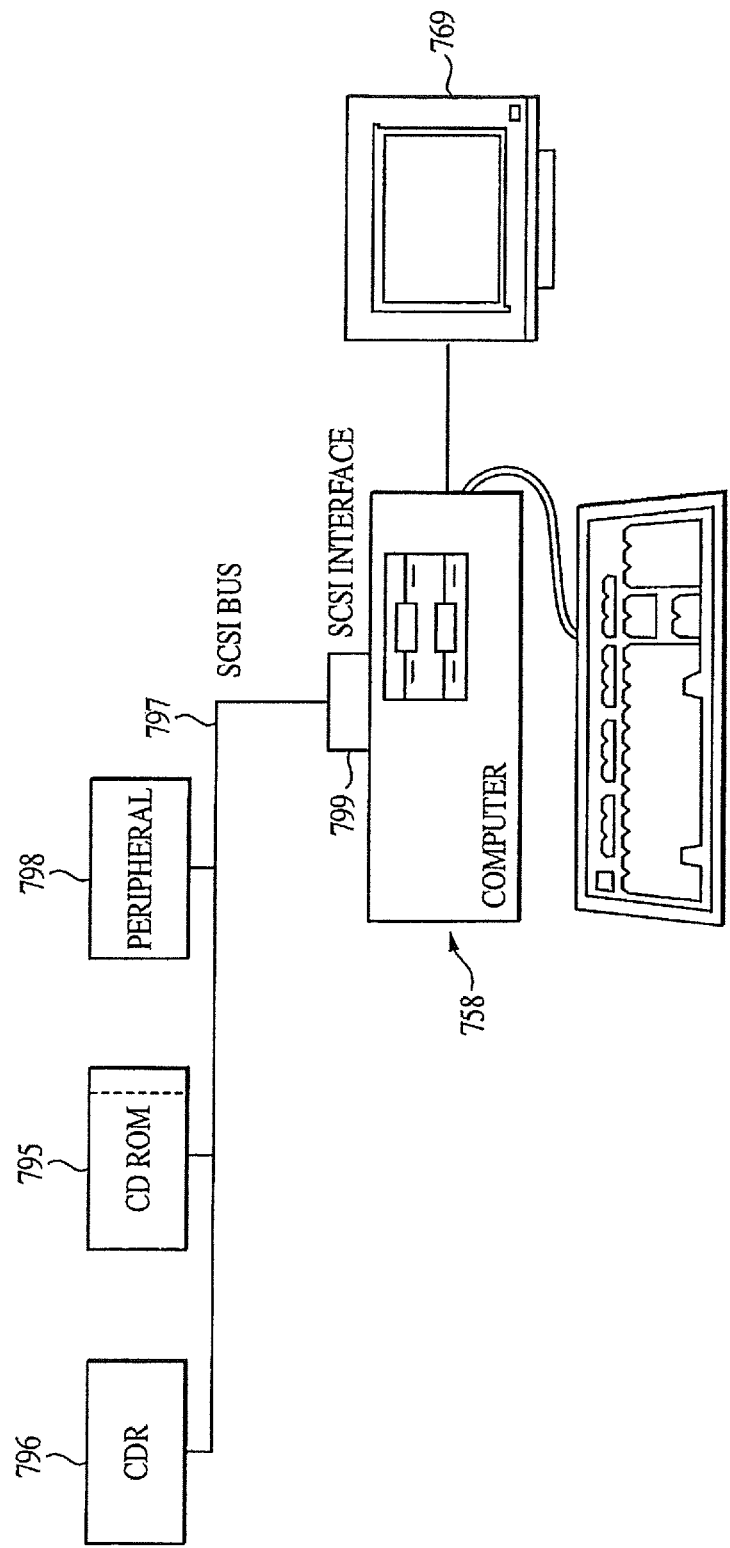
FIG. 22 illustrates a block diagram of an alternate embodiment of a computer used for implementing the computer processing in accordance with a computer-implemented embodiment of the present invention.

Alternatively, referring to FIG. 22, computer 758 may also include a CD ROM reader 795 and CD recorder 796, which are interconnected by a bus 797 along with other peripheral devices 98 supported by the bus structure and protocol. Bus 797 serves as the main information highway interconnecting other components of the computer. It is connected via an interface 799 to the computer 758.

Figure 21:
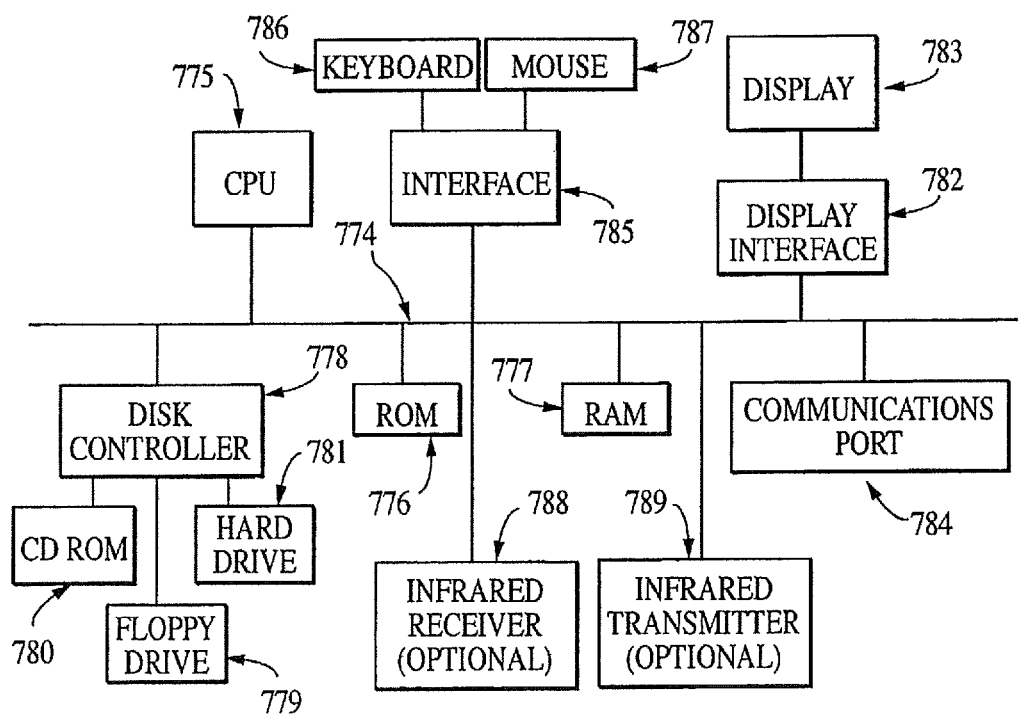
FIG. 21 illustrates a block diagram of the internal hardware of a computer.

FIG. 21 illustrates a block diagram of the internal hardware of the computer of FIG. 20. CPU 775 is the central processing unit of the system, performing calculations and logic operations required to execute a program. Read only memory (ROM) 776 and random access memory (RAM) 777 constitute the main memory of the computer. Disk controller 778 interfaces one or more disk drives to the system bus 774. These disk drives may be floppy disk drives such as 779, or CD ROM or DVD (digital video/versatile disk) drives, as at 780, or internal or external hard drives 781. As previously indicated these various disk drives and disk controllers are optional devices.

A display interface 782 permits information from bus 774 to be displayed on the display 783. Again, as indicated, the display 783 is an optional accessory for a central or remote computer in the communication network, as are infrared receiver 788 and transmitter 789. Communication with external devices occurs using communications port 84.

In addition to the standard components of the computer, the computer may also include an interface 785, which allows for data input through the keyboard 786 or pointing device, such as a mouse 787.

In general, it should be emphasized that various components of embodiments of the present invention can be implemented in hardware, software or a combination thereof. In such embodiments, the various components and steps are implemented in hardware and/or software to perform the functions of the present invention. Any presently available or future developed computer software language and/or hardware components can be employed in such embodiments of the present invention. For example, at least some of the functionality mentioned above could be implemented using the C, C++, or any assembly language appropriate in view of the processor(s) being used. It could also be written in an interpretive environment such as Java and transported to multiple destinations to various users.

Although various embodiments that incorporate the teachings of the present invention have been shown and described in detail herein, those skilled in the art can readily devise many other varied embodiments that incorporate these teachings.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction illustrated and described, and accordingly, all suitable modifications and equivalence may be resorted to, falling within the scope of the invention.

What is claimed is:

1. A method comprising:
reducing a label size of a label into a reduced orientation having a surface securing section exposed therefrom, wherein the label includes label information regarding a medication;
applying a surface securing adhesive to the surface securing section of the label;
securing the label in the reduced orientation;
scanning a label barcode included on the label and scanning a product barcode associated with the medication to facilitate correct matching of the label information with the corresponding medication; and
when the label barcode matches the product barcode, attaching the surface securing section of the label to a surface of a container including the medication, wherein the surface securing adhesive affixes the label to the container.

2. The method of claim 1, wherein the label is between 11 inches and 12 inches in length and between 1.25 inches and 1.75 inches in width.

3. The method of claim 1, wherein the label includes a customer information section, a medication information section, a medication use instructions section, the surface securing section, and a label barcode section.

4. The method of claim 1, wherein the surface securing section is between 1.5 inches and 1.75 inches in length and between 1.25 inches and 1.75 inches in width.

5. The method of claim 1, wherein reducing the label size comprises:
rolling the label; and
creasing the label during rolling, creasing the label after rolling, or creasing the label during rolling and after rolling.

6. The method of claim 5, further comprising:
applying a label securing adhesive to a label securing section of the label, such that the label is secured in a rolled shape by attaching the label securing section to an inner portion of the label that confronts the label securing section.

7. The method of claim 6, wherein the label securing adhesive enables the label to be unrolled and resecured in the rolled shaped without damaging the label.

8. The method of claim 6, wherein the label includes a customer information section, a medication information section, a medication use instructions section, the label securing section, the surface securing section, and a label barcode section.

9. The method of claim 8, wherein the label securing section is between 0.75 inches and 1 inch in length and between 1.25 inches and 1.75 inches in width.

10. The method of claim 8, wherein the surface securing section is between 1.5 inches and 1.75 inches in length and between 1.25 inches and 1.75 inches in width.

11. The method of claim 5, wherein the surface securing adhesive is used to secure the label in a rolled orientation.

12. The method of claim 5, wherein the label is rolled such that an overhanging flap is formed.

13. The method of claim 1, wherein the surface securing adhesive is applied to a first end of the label, such that the label is capable of being unrolled while remaining attached to the container at the first end of the label.

14. The method of claim 1, wherein the surface securing adhesive is applied to the label in a contiguous location on the surface securing section of the label.

15. The method of claim 1, wherein the surface securing adhesive is applied to the label in at least two disparate locations on the surface securing section.

16. The method of claim 1, wherein the label is folded such that a first end and a second end of the label are left exposed.

17. The method of claim 16, wherein the surface securing adhesive is applied to a first surface securing section located at the first end of the label, such that the label is capable of being affixed to the container at the first end of the label.

18. The method of claim 16, wherein the surface securing adhesive is applied to a first surface securing section located at the first end and to a second surface securing section located at the second end of the label, such that the label is capable of being affixed to the container at the first end and the second end of the label.

19. The method of claim 1, further comprising:
printing the label information and the label barcode on the label.

20. The method of claim 1, wherein scanning of the label barcode is performed before the label has been attached to the container.

21. The method of claim 1, wherein scanning of the label barcode is performed after the label has been attached to the container.

22. The method of claim 1, wherein the product barcode of the medication is affixed to the medication, the container, or both the medication and the container, and wherein the label is attached to the container such that the label does not obscure the product barcode.

* * * * *